United States Patent
Gokel et al.

(10) Patent No.: US 10,463,044 B2
(45) Date of Patent: Nov. 5, 2019

(54) MOLECULES THAT INHIBIT EFFLUX PUMPS IN MULTI-DRUG RESISTANT BACTERIA AND USES THEREOF

(71) Applicant: The Curators of the University of Missouri, Columbia, MO (US)

(72) Inventors: George W. Gokel, St. Louis, MO (US); Michael R. Gokel, St. Louis, MO (US); Saeedeh Negin, St. Louis, MO (US); Mohit B. Patel, St. Louis, MO (US)

( * ) Notice: Subject to any disclaimer, the term of this patent is extended or adjusted under 35 U.S.C. 154(b) by 0 days.

(21) Appl. No.: 15/186,070

(22) Filed: Jun. 17, 2016

(65) Prior Publication Data

US 2016/0361292 A1    Dec. 15, 2016

Related U.S. Application Data

(63) Continuation-in-part of application No. PCT/US2015/034550, filed on Jun. 5, 2015.

(60) Provisional application No. 62/008,956, filed on Jun. 6, 2014.

(51) Int. Cl.
| | |
|---|---|
| *A01N 43/72* | (2006.01) |
| *A61K 45/06* | (2006.01) |
| *A61K 31/165* | (2006.01) |
| *A61K 31/395* | (2006.01) |
| *A61K 31/496* | (2006.01) |
| *A61K 31/65* | (2006.01) |
| *A61K 38/16* | (2006.01) |

(52) U.S. Cl.
CPC ............ *A01N 43/72* (2013.01); *A61K 31/165* (2013.01); *A61K 31/395* (2013.01); *A61K 31/496* (2013.01); *A61K 31/65* (2013.01); *A61K 45/06* (2013.01); *A61K 38/16* (2013.01); *A61K 2300/00* (2013.01); *Y02A 50/473* (2018.01)

(58) Field of Classification Search
CPC ....... A61K 45/06; A61K 31/165; A01N 43/72
USPC .................................................. 1/1; 424/405
See application file for complete search history.

(56) References Cited

U.S. PATENT DOCUMENTS

| | | |
|---|---|---|
| 4,783,528 A | 11/1988 | Gokel |
| 5,000,958 A | 3/1991 | Fountain et al. |
| 8,389,505 B2 | 3/2013 | Kralj et al. |
| 2002/0035061 A1 | 3/2002 | Krieger et al. |
| 2009/0062221 A1 | 3/2009 | Dow et al. |
| 2010/0222268 A1 | 9/2010 | Hoffmann et al. |
| 2011/0257254 A1 | 10/2011 | Kralj et al. |
| 2013/0224258 A1 | 8/2013 | Baker |
| 2017/0347652 A1 | 12/2017 | Gokel et al. |

FOREIGN PATENT DOCUMENTS

WO    2015/188140 A1    12/2015

OTHER PUBLICATIONS

Schlecht, title: Overview of antibacterial drgus—Infectious disease; Merck mannuals. Jan. 2005.*
Poole, et al.; title: Efflux pumps as antimicrobial resistance mechanisms; Ann Med. ; vol. 39(3), pp. 162-176, 2007.*
Gokel et al., "Lariat Ethers in Membranes and as Membranes", Bioorganic Chemistry Frontiers, 1990, pp. 115-141, vol. 1.
International Search Report and Written Opinion for PCT/US2015/34550 dated Aug. 26, 2015.
Leevy et al., "Synthetic Hydraphile Channels of Appropriate Length Kill *Escherichia coli*", Journal of the American Chemical Society, 2002, pp. 9022-9023, vol. 124.
Lomovskaya et al., "Identification and Characterization of Inhibitors of Multidrug Resistance Efflux Pumps in Pseudomonas aeruginosa: Novel Agents for Combination Therapy", Antimicrobial Agents and Chemotherapy, Jan. 2001, pp. 105-116, vol. 45, No. 1.
Mahamoud et al., "Antibiotic Efflux Pumps in Gram-Negative Bacteria: The Inhibitor Response Strategy", Journal of Antimicrobial Chemotherapy, 2007, pp. 1223-1229, vol. 59.
Murray et al., "Cation Flux Dependence on Carbon Chain Length in Hydraphile Channels as Assessed by Dynamic 23Na NMR Methods in Phospholipid Bilayers", Chemical Communications, 1998, pp. 2477-2478.
Murray et al., "Spacer Chain Length Dependence in Hydraphile Channels: Implications for Channel Position Within Phospholipid Bilayers", Journal of Supramolecular Chemistry, 2001, pp. 23-30, vol. 1.
Poole, "Efflux-Mediated Multiresistance in Gram-Negative Bacteria", Clinical Microbiology and Infection, Jan. 2004, pp. 12-26, vol. 10, No. 1.
Weber et al., "Dynamic Assessment of Bilayer Thickness by Varying Phospholipid and Hydraphile Synthetic Channel Chain Lengths", Journal of the Ameican Chemical Society, 2005, pp. 636-642, vol. 127.
Halwani et al., "Liposomal Bismuth-Ethanedithiol Formulation Enchances Antimicrobial Activity of Tobramycin", International Journal of Pharmaceutics, Jun. 24, 2008, pp. 278-284, vol. 358, Issues 1-2.
Office Action for U.S. Appl. No. 15/316,344 dated Feb. 7, 2018.
Leevy et al., "Correlation of Bilayer Membrane Cation Transport and Biological Activity in Alkyl Substituted Lariat Ethers", Org. Biomol. Chem., 2005, pp. 1647-1652, vol. 3.

* cited by examiner

*Primary Examiner* — Yanzhi Zhang
(74) *Attorney, Agent, or Firm* — Thompson Coburn LLP; William A. Holtz

(57) ABSTRACT

Methods and compositions are provided for increasing or enhancing the efficacy of antibiotics, such as by increasing antimicrobial activity, against a variety of microbes by co-administration with synthetic amphiphiles, including lariat ethers and hydraphiles. Methods and compositions for overcoming antibiotic resistance are also provided.

8 Claims, 22 Drawing Sheets

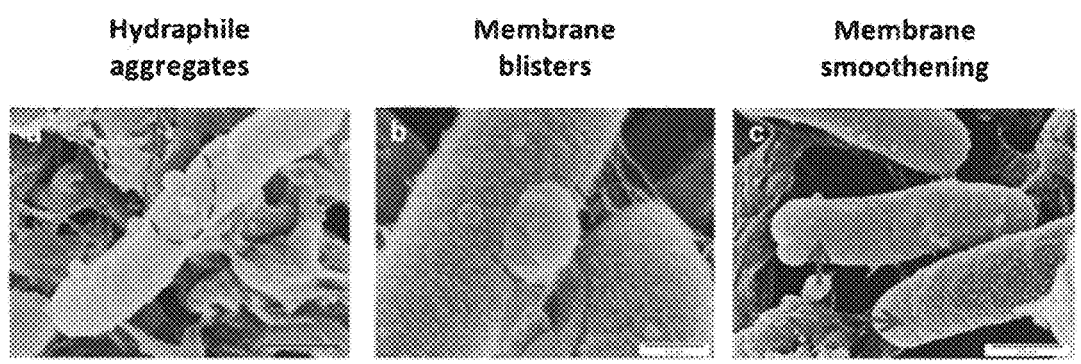
FIGURE 20A/B/C

MOLECULES THAT INHIBIT EFFLUX PUMPS IN MULTI-DRUG RESISTANT BACTERIA AND USES THEREOF

CROSS REFERENCE TO RELATED APPLICATIONS

This application is a bypass Continuation-In-Part (CIP) application of International Application No. PCT/US2015/034550, filed Jun. 5, 2015, which claims the benefit of U.S. Provisional Application Ser. No. 62/008,956, filed Jun. 6, 2014, contents of which are hereby incorporated by reference in their entireties.

GOVERNMENT RIGHTS STATEMENT

This invention was made with government funding under Grant No. CHE 1307324, provided by the National Science Foundation (NSF). The government has certain rights in the invention.

BACKGROUND

Certain synthetic amphiphiles are known to exhibit toxicity to microbes such as Gram negative *Escherichia coli*, Gram positive *Bacillus subtilis*, and the yeast *Saccharomyces cerevisiae*. The minimum inhibitory concentrations (MICs) of such synthetic amphiphiles against the various microbes depend on the microbe per se and on the structure of the synthetic amphiphile.

Combination drugs such as amoxicillin and clavulanic acid, sold as AUGMENTIN®, and piperacillin and tazobactam, sold as ZOSYN®, are effective antimicrobials. Certain amphiphilic calixarene molecules have been prepared with integral antibiotic elements, but these comprise prodrugs rather than combination therapies as described in *Bioorganic and Medicinal Chemistry* 2012, 20, 2035-2041.

Antibiotic resistance has become a major health crisis. Since 1940, the increasing and sometimes frivolous use of antibiotics has led to a dangerous level of bacterial resistance (a. Center for Disease Control and Prevention, Antibiotic resistance threats in United States, 2013. b. World Health Organization, Antimicrobial resistance global report and surveillance, 2014). Bacterial resistance has been identified to the all known classes of antibiotics. Cultured bacteria are used to identify new antibiotics. Recently two new antibiotics: teixobactin and Aspergillomarasmine A have been invented using this technique. Antibiotics such as teixobactin are of greater significance because it is difficult for the bacteria to develop resistance to them.

Efflux pump function provides a general resistance mechanism that affects multiple different classes of antibiotics (Poole, K.; *Clinic. Microbiol. Infec.* 2004, 10, 12-26). Acquisition of efflux pump based resistance usually leads to the acquisition of other types of resistance mechanisms (target mutation and antibiotic-degrading enzymes). However, such mechanisms contribute independently to resistance development (Lomovskaya, et al., *Antimicrob. Agents Chemother.*, 2001, 45, 105-116). All the efflux pumps utilize either a cation gradient (proton or sodium) or hydrolyzes an ATP molecule for active antibiotic transport (McNicholas, et al., *J. Bacteriol.*, 1992, 174, 7926-7933; Levy, S. B., *Antimicrob. Agent. Chemo.*, 1992, 36, 695-703). The second membrane in Gram-negative bacteria provide a reduced influx of antibiotics in to the cell. Hence, the antimicrobial resistance (AMR) in Gram-negative bacteria is a combination of reduced influx and increased efflux of antibiotics (Zgurskaya, et al., *ACS Infect. Dis.* 2015, DOI:10.1021/acsinfecdis.5b00097). The majority of the ESKAPE pathogens are Gram-negative pathogens, causing serious illness (Nikaido, H., Science, 1994, 264, 382-388). Numerous approaches have been reported for increasing antibiotic concentration in the cell cytoplasm of efflux pump expressing bacteria (Mahamoud, et al., *J. Antimicrob. Chemoth.* 2007, 59, 1223-1229). For example, Phenylalanine arginyl β-naphthylamide (PAβN) recovers levofloxacin efficacy against *Pseudomonas aeruginosa* (Lomovskaay, et al., *Antimicrob. Agents Chemother.* 2001, 45, 105-116). However, there is no report to date of such adjuvants that can prevent resistance development by bacteria.

There is a need for new compounds that can act as antimicrobials and a need for methods to recover or enhance efficacy of existing antimicrobial agents and to combat increasing microbe resistance to antibiotics.

SUMMARY

Disclosed herein are various embodiments of a method of enhancing the antimicrobial activity of an antibiotic. In certain embodiments, a method comprises administering to a microbe the antibiotic with a synthetic amphiphile. In certain embodiments, the synthetic amphiphile is a compound comprising one or more polar head groups in which each polar head group comprises at least three oxygen and hydrocarbon residues as the nonpolar elements. In certain embodiments, the synthetic amphiphile is a lariat ether or a hydraphile. In certain embodiments, the antibiotic and synthetic amphiphile are administered to the microbe such as by contacting the microbe in culture or in solution or by applying the antibiotic and synthetic amphiphile to a material, such as the surface of a material, in or on which the microbe resides. In certain embodiments, the method increases the antimicrobial activity of the antibiotic by about 2-fold to about 40-fold.

In certain embodiments, the synthetic amphiphile is a lariat ether. In certain embodiments, the synthetic amphiphile is a lariat ether and the lariat ether comprises a diaza-18-crown-6 macrocycle and two linear alkyl chains ranging in length from 1 to 20 carbon atoms, or from 1 to 22 carbon atoms. In certain embodiments, the synthetic amphiphile is a lariat ether and the lariat ether comprises a diaza-15-crown-5 macrocycle and two linear alkyl chains ranging in length from 1 to 20 carbon atoms, or from 1 to 22 carbon atoms. In certain embodiments, the synthetic amphiphile is a lariat ether and the lariat ether is N,N'-di-n-octyl-4,13-diaza-18-crown-6. In certain embodiments, the synthetic amphiphile is a lariat ether and the lariat ether is N,N'-di-n-decyl-4,13-diaza-18-crown-6. In certain embodiments, the synthetic amphiphile is a lariat ether and the lariat ether is N,N'-di-n-undecyl-4,13-diaza-18-crown-6. In certain embodiments, the synthetic amphiphile is a lariat ether and the lariat ether is N,N'-di-n-dodecyl-4,13-diaza-18-crown-6. In certain embodiments, the synthetic amphiphile is a lariat ether and the lariat ether is N,N'-di-n-tetradecyl-4,13-diaza-18-crown-6. In certain embodiments, the synthetic amphiphile is a lariat ether and the lariat ether does not comprise an adamantyl group.

In certain embodiments, the synthetic amphiphile is a hydraphile. In certain embodiments, the synthetic amphiphile is a hydraphile and the hydraphile comprises the structure of Formula 4:

Formula 4

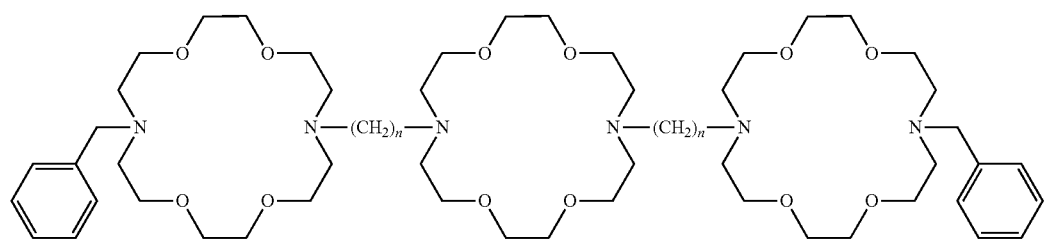

wherein n is 6. In certain embodiments, the synthetic amphiphile is a hydraphile and the hydraphile comprises the structure of Formula 4:

Formula 4

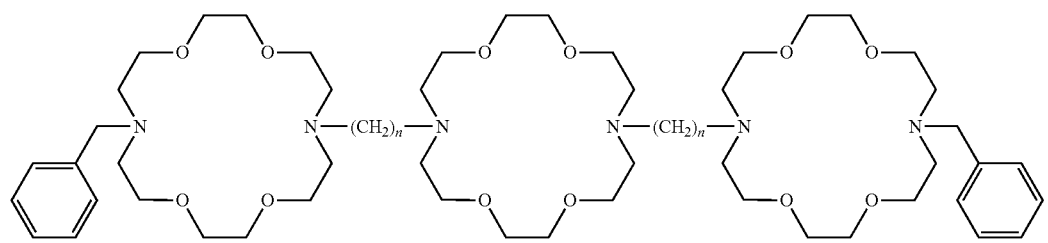

wherein n is 8. In certain embodiments, the synthetic amphiphile is a hydraphile and the hydraphile comprises the structure of Formula 4:

Formula 4

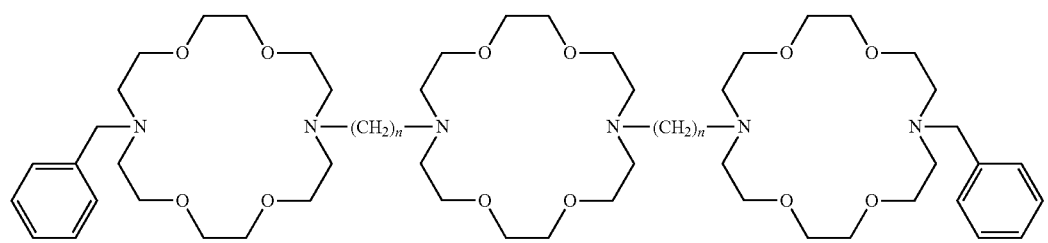

wherein n is 10. In certain embodiments, the synthetic amphiphile is a hydraphile and the hydraphile comprises the structure of Formula 2:

Formula 2

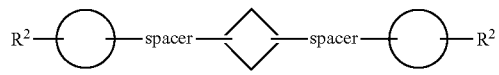

wherein the macrocycles (open circles) are 4,10-diaza-15-crown-5, the spacers are n-dodecylene, and the side chains ($R^2$) are n-dodecyl. The diamond (middle between spacers) represents a polar structural element. In certain embodiments, the polar structural element is a macrocycle. Compounds 3 and 7 as shown in FIG. 10 are representative hydraphiles in which the polar element is not a macrocycle but rather a triethyleneoxy unit or an amide-containing module.

In certain embodiments, the microbe is a bacterium. In certain embodiments, the microbe is a bacterium in the family Enterobacteriaceae, in the family Bacillaceae, or in the family Pseudomonadaceae. In certain embodiments, the bacterium is *Escherichia coli* (*E. coli*). In certain embodiments, the microbe is a bacterium that is resistant to the antibiotic. In certain embodiments, the bacterium is an antibiotic resistant *E. coli*.

In the present context, antibacterial and antimicrobial are understood to mean any compound that either inhibits or completely arrests or prevents microbial growth or kills the microbe.

In certain embodiments, the antibiotic, the synthetic amphiphile, or both the antibiotic and the synthetic amphiphile are administered at a concentration below their minimum inhibitory concentrations. In certain embodiments, the antibiotic is administered at a concentration below its minimum inhibitory concentration. In certain embodiments, the synthetic amphiphile is administered at a concentration below its minimum inhibitory concentration. In certain embodiments, both the antibiotic and the synthetic amphiphile are administered at concentrations below their minimum inhibitory concentrations when determined in the absence of the second additive. In certain embodiments, the antibiotic is administered to a concentration of about 0.1 μM to about 400 μM. In certain embodiments, the synthetic amphiphile is administered to a concentration of about 0.1 μM to about 400 μM. In certain embodiments, the antibiotic is administered to a concentration of about 0.1 μM to about 400 μM and the synthetic amphiphile is administered to a concentration of about 0.1 μM to about 400 μM.

In certain embodiments, the antibiotic is an antibiotic selected from the group consisting of kanamycin, tobramycin, erythromycin, rifampicin, and tetracycline. In certain embodiments, the antibiotic is an antibiotic selected from the group consisting of erythromycin, rifampicin, and tetracycline. In certain embodiments, the antibiotic is kanamycin. In certain embodiments, the antibiotic is tobramycin. In certain embodiments, the antibiotic is erythromycin. In certain embodiments, the antibiotic is rifampicin. In certain embodiments, the antibiotic is tetracycline.

In certain embodiments, the microbe is *E. coli*, the antibiotic is selected from the group consisting of rifampicin, tetracycline, kanamycin, and erythromycin, and the synthetic amphiphile is N,N'-di-n-octyl-4,13-diaza-18-crown-6 lariat ether or N,N'-di-n-undecyl-4,13-diaza-18-crown-6 lariat ether. In certain embodiments, the microbe is a tetracycline resistant strain of *E. coli*, the antibiotic is tetracycline, and the synthetic amphiphile is a hydraphile.

Certain embodiments provide for methods of treating a microbial infection. Such methods comprise administering to a subject suffering from the microbial infection an effective amount of a combination of an antibiotic and a synthetic amphiphile as described herein.

Also disclosed herein is a method of inhibiting efflux pump activity in a multi-drug resistant bacterium by administering to the bacterium with an amphiphile. In certain embodiments, the amphiphile is a compound comprising one or more polar head groups, and wherein each polar head group comprises at least three oxygen and hydrocarbon residues as the nonpolar elements.

Further disclosed herein is a method of selectively increasing permeability of a bacterial cell by administering to the bacterial cell with an amphiphile. In certain embodiments, the amphiphile is a compound comprising one or more polar head groups, and wherein each polar head group comprises at least three oxygen and hydrocarbon residues as the nonpolar elements.

BRIEF DESCRIPTION OF DRAWINGS

FIG. 15A shows resistance developed by $Tet^R$ *E. coli* to minocycline and $C_{14}$ hydraphile. In particular, *E. coli* developed resistance to minocycline but did not develop resistance to $C_{14}$ hydraphile beyond 4 μM in 15 days.

FIG. 16A shows accumulation of ethidium bromide in the presence of reserpine, CCCP, $C_8$-$C_{14}$ hydraphiles (4 μM) in *S. aureus* 1199B expressing NorA efflux pump.

FIG. 17A shows potassium effluxed from the *E. coli* cells in the presence of $C_8$-$C_{14}$ hydraphiles, DMSO (0.1%), gramicidin D and Valinomycin.

FIGS. 20A/B/C show that hydraphiles form aggregates, cause membrane disruption and disrupt ion gradients. FIG. 20A shows uniform hydraphile aggregates attached to the bacterial surface. FIG. 20B shows that disruption of cytoplasmic membrane by hydraphiles forms blisters on the surface of the bacteria. FIG. 20C shows that disruption of ion gradient caused by hydraphile leads to smoothening of bacterial membrane.

DETAILED DESCRIPTION

It is to be noted that the term "a" or "an" entity refers to one or more of that entity; for example, "an antibiotic" is understood to represent one or more antibiotics. As such, the terms "a" (or "an"), "one or more," and "at least one" can be used interchangeably herein.

Unless defined otherwise, all technical and scientific terms used herein have the same meaning as commonly understood by one of ordinary skill in the art to which this disclosure is related.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole.

It has been discovered that the combination of certain synthetic amphiphiles with a range of antimicrobial agents, such as antibiotics, shows unexpectedly enhanced efficacy, increased activity, etc., of the antimicrobial agents against a range of organisms, including in some cases those microbes that are resistant to a particular antimicrobial agent. It has further been discovered that certain hydraphiles that are too short to form ion-conducting channels surprisingly and unexpectedly also enhanced antimicrobial activity. It was also discovered that organisms that are resistant to certain antimicrobial agents succumb to that antimicrobial agent when the antimicrobial agent and one or more synthetic amphiphiles, such as those described herein, is co-administered with the antimicrobial agent.

Lariat ethers are compounds known in the art as cation complexing agents such as described in U.S. Pat. Nos. 4,436,664, 4,474,963, 4,597,903, and 4,687,844. Lariat ethers contain a macrocyclic ring and one or more side arms as described herein. A macrocycle is a ring compound comprising at least 9-members, but more typically 12 or more atoms connected together. Macrocyclic rings at least as large as 60 atoms are also known in the art. Lariat ethers are characterized by a macrocyclic ring having from 12-48 members and containing heteroatoms including, but not limited to, oxygen, nitrogen and sulfur. Lariat ethers possess one or more side arms or side chains attached to the macrocyclic ring. The attachment of the side chains can be at carbon, nitrogen, or sulfur or any combination thereof within the ring. Heteroatoms such as oxygen, nitrogen, and sulfur can also be present in the side arms. The side arms can be linear or branched alkyl, unsaturated alkyl, aralkyl, aryl, or heteroaryl, and heteroatoms such as oxygen, nitrogen, and/or sulfur can be present in or attached to the aralkyl, aryl, or heteroaryl portions of the side chains. Lariat ethers are known to be amphiphiles as described in *Advances in Bio-organic Frontiers*; H. Dugas, Springer Verlag: Berlin, 1990; Vol. 1; pp 116-141.

Figure 10:
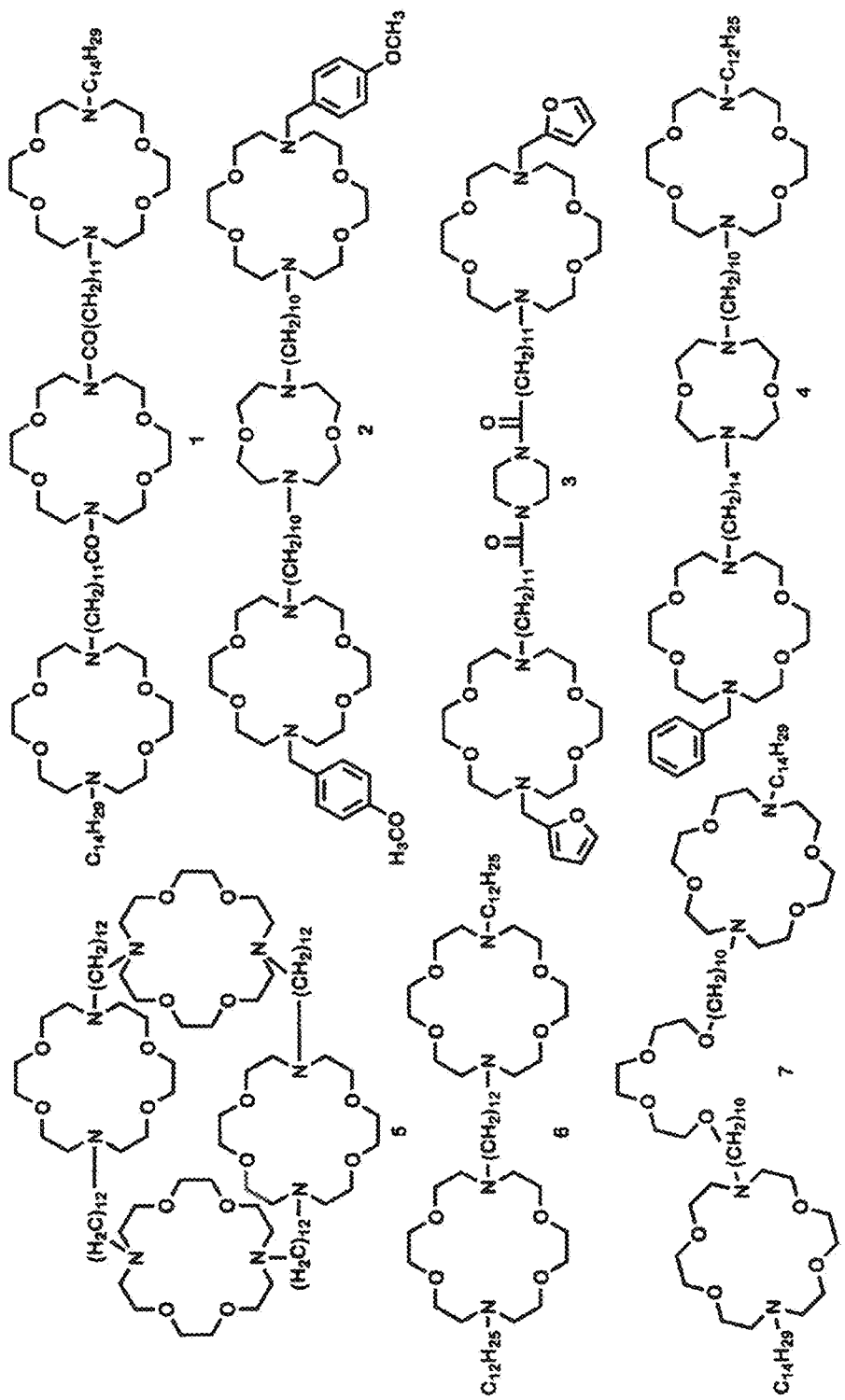
FIG. 10 shows seven representative examples of chemical structures of hydraphiles and hydraphile-like compounds.

Hydraphiles are synthetic amphiphiles known in the art such as described in *Chemical Communications* 2000, 1-9. Hydraphiles are typically composed of three macrocyclic rings, separated by organic spacer elements, and terminated by various side arms. In certain embodiments, the side arm can be hydrogen attached to a nitrogen heteroatom. The spacer chains can contain 1-30 carbon atoms and can be saturated or unsaturated, linear or branched, including aromatic and heteroaromatic residues. The side arms can be linear or branched alkyl, unsaturated alkyl, aralkyl, aryl, or heteroaryl and the spacer chains can contain heteroatoms such as oxygen, nitrogen, and/or sulfur. Hydraphiles have also been prepared that have two (e.g., 3, 7) and four (e.g., 5) macrocyclic rings that function as pore-formers in bilayer membranes as shown in FIG. 10.

Figure 11:
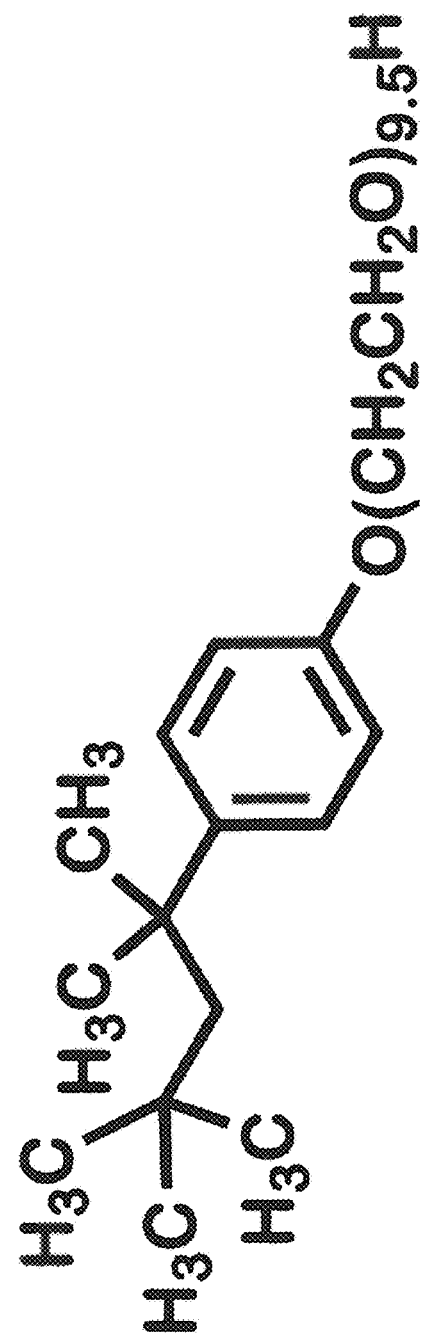
FIG. 11 shows the chemical structure of TRITON X-100.

Amphiphiles are compounds that have both polar and non-polar elements. A synthetic amphiphile as understood herein is a compound that contains at least one polar element or "head group" and at least one nonpolar element or "tail." TRITON X-100, shown in FIG. 11, is one representative example. The compound numbered 7 in FIG. 10 is another representative example and has two polar macrocycles and a triethyleneoxy group that can also serve as a polar head group.

Figure 1:
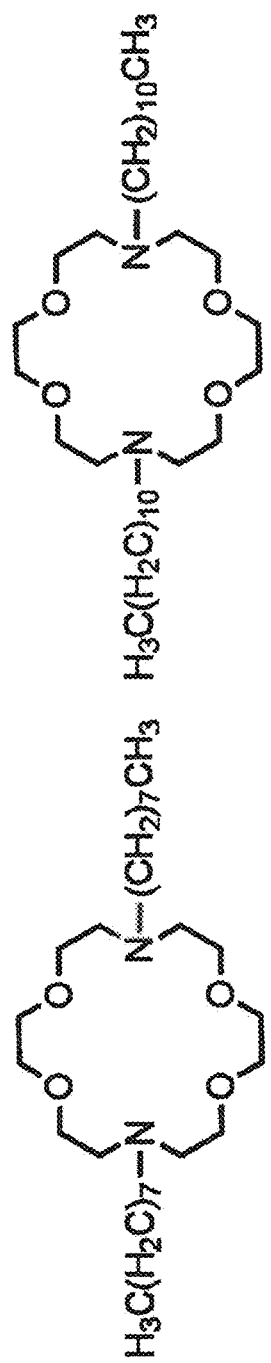
FIG. 1 illustrates chemical structures of N,N'-di-n-octyl-4,13-diaza-18-crown-6 and N,N'-di-n-undecyl-4,13-diaza-18-crown-6, which are exemplified in the present disclosure.

An example of a synthetic amphiphile is the detergent sold as TRITON X-100 (FIG. 11) in which the hydrocarbon residue is nonpolar and the oligoethylene glycol portion is polar. Certain embodiments are directed to synthetic amphiphiles such as, but not limited to, N,N'-di-n-undecyl-4,13-diaza-18-crown-6. In this compound, the 18-membered macrocyclic ring possesses six heteroatoms (four oxygens and two nitrogens) that render the cyclic structure polar. The two 11-carbon chains attached to the two macrocyclic ring nitrogen atoms are hydrophobic and nonpolar and comprise the synthetic amphiphile's nonpolar elements. FIG. 1 is an illustrative example showing the chemical structures of N,N'-bis(n-octyl)-4,13-diaza-18-crown-6 and N,N'-bis(n-undecyl)-4,13-diaza-18-crown-6. It is understood, however, that the methods described herein are not limited to the synthetic amphiphiles illustrated in FIG. 1.

Certain aspects are drawn to a method for increasing or enhancing the antimicrobial activity of an antimicrobial agent. As used herein, the "antimicrobial activity" of an antimicrobial agent is defined as the property of a substance to inhibit the growth and reproduction of a microbial organism or to kill it. Common terms generally applied to bacteria are bacteriostatic (stops growth) and bactericidal (kills bacteria). Depending on the concentrations applied, microbial growth can be slowed or stopped in comparison to concurrent experiments conducted in the absence of an antimicrobial agent. Depending on the concentrations applied, additional microbe death can occur in comparison to concurrent experiments conducted in the absence of an antimicrobial agent. The results of minimum inhibitory concentration (MIC) evaluations and growth curves are presented herein and the conditions are specified. The MIC is the lowest concentration of any agent having antimicrobial activity that inhibits the growth of a microorganism as judged by visual inspection. MIC can be determined by inoculating media with the organism and adding the antimicrobial agent diluted successively in half. After an appropriate incubation time, the MIC is evaluated by inspection as the transition between two successive 2-fold dilutions in which the one concentrated sample is clear and growth is apparent in the 2-fold less concentrated sample. Reference herein to increasing or enhancing activity, efficacy, potency, and the like are used interchangeably to mean that when the synthetic amphiphile is present, the ability of the antimicrobial agent to inhibit the growth of or to kill an organism will be manifested at a concentration lower than would be required to achieve the same results in the absence of said synthetic amphiphile. In certain embodiments, the method increases the antimicrobial activity of the antibiotic by: about 2-fold to about 40-fold; by about 5-fold to about 40-fold; by about 10-fold to about 40-fold; by about 15-fold to about 40-fold; by about 20-fold to about 40-fold; by about 25-fold to about 40-fold; by about 30-fold to about 40-fold, by about 35-fold to about 40-fold; or by about 40-fold. In certain embodiments, the method increases the antimicrobial activity of the antibiotic: by about 2-fold to about 48-fold; by about 5-fold to about 48-fold; by about 10-fold to about 48-fold; by about 15-fold to about 48-fold; by about 20-fold to about 48-fold; by about 25-fold to about 48-fold; by about 30-fold to about 48-fold; by about 35-fold to about 48-fold; by about 40-fold to about 48-fold; or by about 48-fold. In certain embodiments, the method increases the antimicrobial activity of the antibiotic: by about 2-fold to about 50-fold; by about 5-fold to about 50-fold; by about 10-fold to about 50-fold; by about 15-fold to about 50-fold; by about 20-fold to about 50-fold; by about 25-fold to about 50-fold; by about 30-fold to about 50-fold; by about 35-fold to about 50-fold; by about 40-fold to about 50-fold; by about 50-fold, or greater than about 50-fold.

Figure 2:
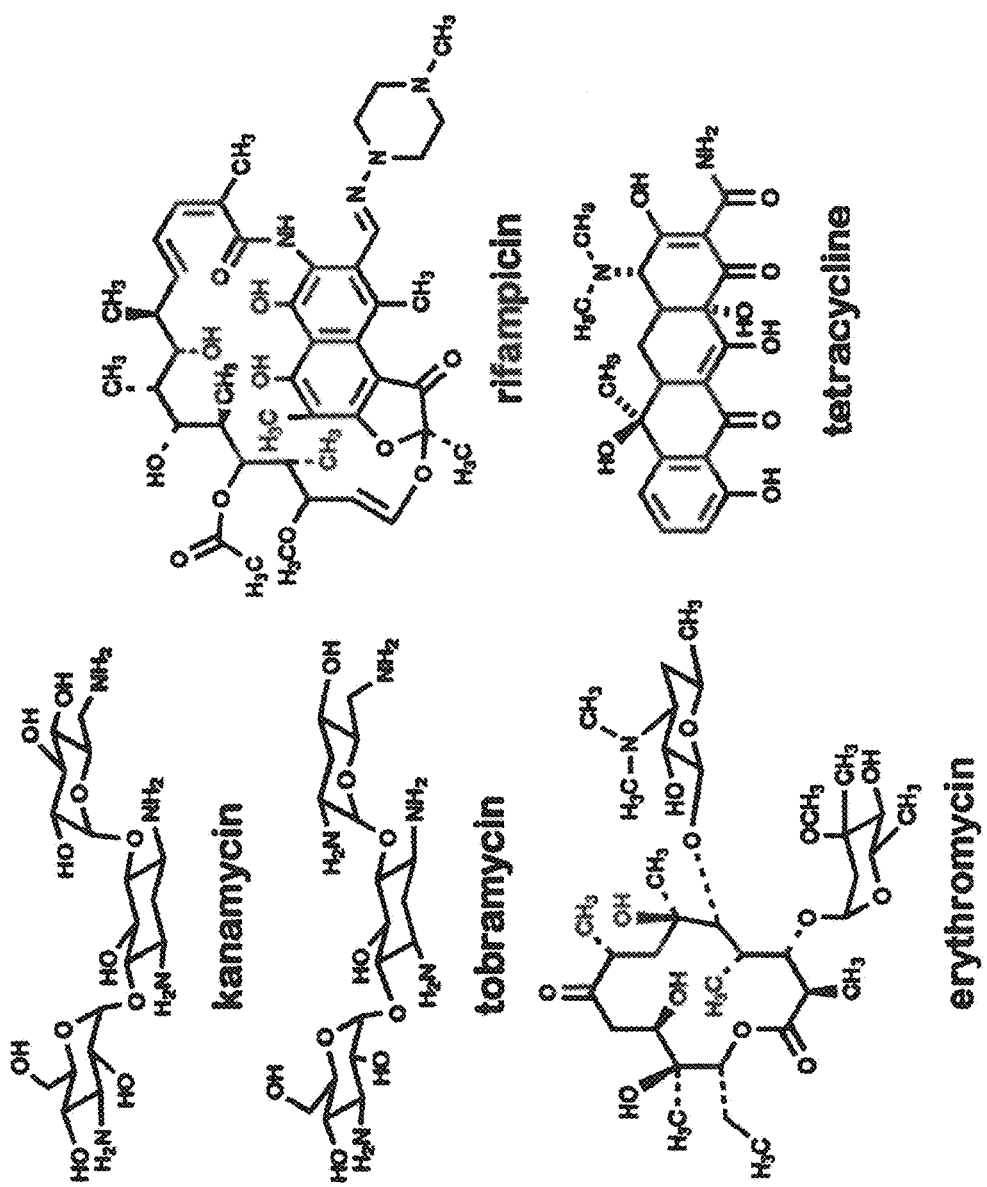
FIG. 2 illustrates chemical structures of five antibiotics that are exemplified in the present disclosure.

In certain embodiments, the antimicrobial agent is an antibiotic. The structures of five illustrative antibiotics are shown in FIG. 2 (i.e., kanamycin, tobramycin, erythromycin, rifampicin, and tetracycline). It is understood that the methods described herein are not limited to the antibiotics illustrated in FIG. 2. Other antibiotics are exemplified herein and numerous other antibiotics, too numerous to list, are contemplated. For example, the following is a brief list of some compounds that are within the scope of the disclosure: Carbapenems such as Imipenem, Meropenem, Ertapenem, Doripenem, and Biapenem; penicillins, cephalosporins (Cefoxitin), glycopeptides (vancomycin), macrolides (azithromycin, clarithromycin), quinolones (ciprofloxacin, naldixic acid), sulfamides (sulfadiazine), isoniazid, and streptomycin. In certain embodiments, the antibiotic is administered to a concentration of:

about 0.001 µM to about 400 µM;
about 0.001 µM to about 300 µM;
about 0.001 µM to about 200 µM;
about 0.001 µM to about 100 µM;
about 0.001 µM to about 50 µM;
about 0.001 µM to about 25 µM;
about 0.001 µM to about 10 µM;
about 0.001 µM to about 1 µM;
about 0.001 µM to about 0.1 µM; or
about 0.001 µM to about 0.01 µM.

In certain embodiments, the antibiotic is administered to a concentration of:

about 0.01 µM to about 400 µM;
about 0.01 µM to about 300 µM;
about 0.01 µM to about 200 µM;
about 0.01 µM to about 100 µM;
about 0.01 µM to about 50 µM;
about 0.01 µM to about 25 µM;
about 0.01 µM to about 10 µM;
about 0.01 µM to about 1 µM; or
about 0.01 µM to about 0.1 µM.

In certain embodiments, the antibiotic is administered to a concentration of:

about 0.1 µM to about 400 µM;
about 0.1 µM to about 300 µM;
about 0.1 µM to about 200 µM;
about 0.1 µM to about 100 µM;
about 0.1 µM to about 50 µM;
about 0.1 µM to about 25 µM;
about 0.1 µM to about 10 µM; or
about 0.1 µM to about 1.0 µM.

In certain embodiments, the antibiotic is administered to a concentration of:

about 0.001 µM to about 400 µM;
about 0.01 µM to about 400 µM;
about 0.1 µM to about 400 µM;
about 1.0 µM to about 400 µM;
about 10 µM to about 400 µM;
about 100 µM to about 400 µM;
about 200 µM to about 400 µM;
about 300 µM to about 400 µM;
about 0.001 µM to about 300 µM;
about 0.01 µM to about 300 µM;
about 0.1 µM to about 300 µM;
about 1.0 µM to about 300 µM;
about 10 µM to about 300 µM;
about 100 µM to about 300 µM;
about 200 µM to about 300 µM;
about 0.001 µM to about 200 µM;
about 0.01 µM to about 200 µM;
about 0.1 µM to about 200 µM;
about 1.0 µM to about 200 µM;
about 10 µM to about 200 µM;
about 100 µM to about 200 µM;
about 0.001 µM to about 100 µM;
about 0.01 µM to about 100 µM;
about 0.1 µM to about 100 µM;
about 1.0 µM to about 100 µM;
about 10 µM to about 100 µM; or
about 50 µM to about 100 µM.

Certain aspects are drawn to a method for increasing or enhancing the antimicrobial activity of an antimicrobial agent by administering the antimicrobial agent in combination with a synthetic amphiphile. In certain embodiments, the synthetic amphiphile that is capable of increasing or enhancing antimicrobial activity is a lariat ether and/or a hydraphile. In certain embodiments, a synthetic amphiphile is capable of reversing the resistance of a microbe to an antimicrobial agent. In certain embodiments, the synthetic amphiphile that is capable of reversing the resistance of a microbe to an antimicrobial agent is a lariat ether and/or a hydraphile. In certain embodiments, the synthetic amphiphile is administered to a concentration of:

about 0.001 µM to about 400 µM;
about 0.001 µM to about 300 µM;
about 0.001 µM to about 200 µM;
about 0.001 µM to about 100 µM;
about 0.001 µM to about 50 µM;
about 0.001 µM to about 25 µM;
about 0.001 µM to about 10 µM;
about 0.001 µM to about 1 µM;
about 0.001 µM to about 0.1 µM; or
about 0.001 µM to about 0.01 µM.

In certain embodiments, the synthetic amphiphile is administered to a concentration of:

about 0.01 µM to about 400 µM;
about 0.01 µM to about 300 µM;
about 0.01 µM to about 200 µM;
about 0.01 µM to about 100 µM;
about 0.01 µM to about 50 µM;

about 0.01 µM to about 25 µM;
about 0.01 µM to about 10 µM;
about 0.01 µM to about 1 µM; or
about 0.01 µM to about 0.1 µM.

In certain embodiments, the synthetic amphiphile is administered to a concentration of:
about 0.1 µM to about 400 µM;
about 0.1 µM to about 300 µM;
about 0.1 µM to about 200 µM;
about 0.1 µM to about 100 µM;
about 0.1 µM to about 50 µM;
about 0.1 µM to about 25 µM;
about 0.1 µM to about 10 µM; or
about 0.1 µM to about 1.0 µM.

In certain embodiments, the synthetic amphiphile is administered to a concentration of:
about 0.001 µM to about 400 µM;
about 0.01 µM to about 400 µM;
about 0.1 µM to about 400 µM;
about 1.0 µM to about 400 µM;
about 10 µM to about 400 µM;
about 100 µM to about 400 µM;
about 200 µM to about 400 µM;
about 300 µM to about 400 µM;
about 0.001 µM to about 300 µM;
about 0.01 µM to about 300 µM;
about 0.1 µM to about 300 µM;
about 1.0 µM to about 300 µM;
about 10 µM to about 300 µM;
about 100 µM to about 300 µM;
about 200 µM to about 300 µM;
about 0.001 µM to about 200 µM;
about 0.01 µM to about 200 µM;
about 0.1 µM to about 200 µM;
about 1.0 µM to about 200 µM;
about 10 µM to about 200 µM;
about 100 µM to about 200 µM;
about 0.001 µM to about 100 µM;
about 0.01 µM to about 100 µM;
about 0.1 µM to about 100 µM;
about 1.0 µM to about 100 µM;
about 10 µM to about 100 µM; or
about 50 µM to about 100 µM.

It is understood that in certain embodiments, the antibiotic and the synthetic amphiphile can be administered together to the respective concentrations disclosed herein.

Figure 12:
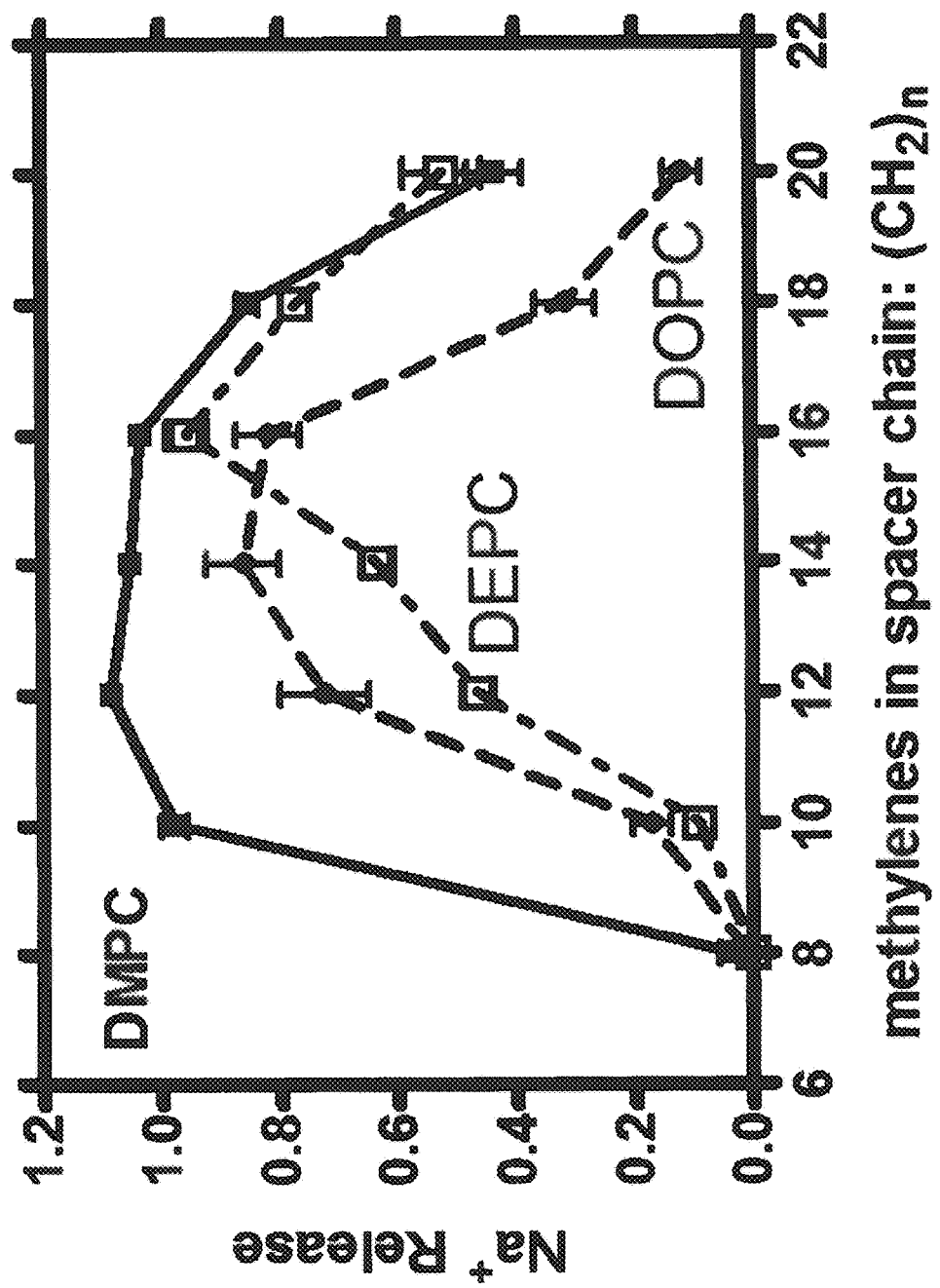
FIG. 12 shows the correspondence between membrane thickness and hydraphile spacer chain length as determined by the percentage of ions released from vesicles.

In certain embodiments, a short-chain hydraphile is used to increase or enhance the potency or antimicrobial activity of an antimicrobial agent. In certain embodiments, a short-chain hydraphile is used to reverse the resistance of a microbe to an antimicrobial agent. Short-chained hydraphiles have spacer chains of such a length that they do not span the lipid bilayer and therefore do not exhibit the property of cation transport by pore formation. The length dependence was demonstrated in *Chemical Communications* 1998, 2477-2478. However, it is well known in the art that the membranes of cells have many different components and thicknesses. It was demonstrated in the *Journal of the American Chemical Society* 2005, 126, 636-642, that the ability of hydraphiles to transport cations depended on the correspondence between membrane thickness and hydraphile spacer chain length. Thus, liposomes were formed from three different phospholipids: 1,2-dimyristoleoyl-sn-glycero-3-phosphocholine (DMPC, shorter fatty acid chains, thinner membranes), 1,2-dioleoyl-sn-glycero-3-phosphocholine (DOPC), and 1,2-dierucoyl-sn-glycero-3-phosphocholine (DEPC, longest fatty acid chains, thickest membranes). The graph of FIG. 12 shows that $C_8$ benzyl hydraphile failed to transport irrespective of whether it was present in DMPC, DOPC, or DEPC membranes. The $C_8$ benzyl hydraphile is a short-chained hydraphile and those compounds having spacer chains shorter than eight linear atoms can also be classified as short-chained hydraphiles. The graph of FIG. 12 also shows that in the thickest DEPC membranes, $C_{10}$ benzyl hydraphile is nearly inactive. Thus, short-chained hydraphiles are those that fail to transport cations by pore formation in the context of the organism's membrane structure. It is known from the *Journal of the American Chemical Society* 2002, 124, 9022-3, that hydraphiles are toxic to *E. coli* in appropriate concentrations. Thus, $C_{12}$ benzyl hydraphile killed *E. coli* but $C_8$ benzyl hydraphile did not.

As used herein, a short-chained hydraphile comprises spacer chains of such a length that they do not span the lipid bilayer of a particular membrane to which the short-chained hydraphiles are contacted and therefore do not exhibit the property of cation transport by pore formation. In certain embodiments, a short-chained hydraphile has spacer chains of ten or less linear atoms. In certain embodiments, a short-chained hydraphile has spacer chains of eight or less linear atoms. In certain embodiments, a short-chained hydraphile has spacer chains of six or less linear atoms.

A general formula for lariat ethers is shown as Formula 1.

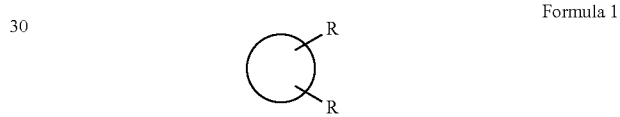

Formula 1

In Formula 1, the circle represents a macrocyclic ring, which can be composed of heteroatoms such as O, N, and/or S. The ring sizes can range from about 12 members to about 48 members. The side arms (R) can be saturated or unsaturated alkyl, saturated or unsaturated aralkyl, aryl or substituted aryl including heteroaromatic groups. The side arms can possess heteroatoms such as oxygen, nitrogen, and/or sulfur. Heteroatoms can also be present in groups appended to the aryl or heteroaryl residues. In certain of any of the embodiments disclosed herein, a lariat ether does not comprise an adamantyl group. In certain of any of the embodiments disclosed herein, an adamantyl group is not incorporated as a terminal residue in a side chain or the side chains of a lariat ether of the embodiments.

A general formula for hydraphiles is shown as Formula 2.

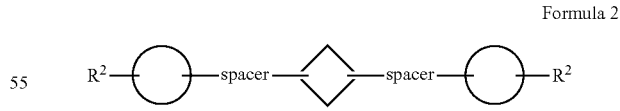

Formula 2

The spacers (also referred to as "spacer chains") can range from 1-30 atoms and can be linear or branched, and can be saturated or unsaturated. The size of the macrocyclic rings can range from about 12 members to about 48 members. The side arms ($R^2$) can be linear or branched, saturated or unsaturated alkyl, saturated or unsaturated aralkyl, aryl or substituted aryl including heteroaromatic groups. The side arms can possess heteroatoms such as oxygen, nitrogen, and/or sulfur. Heteroatoms can also be present in groups appended to the aryl or heteroaryl residues. The diamond (middle between spacers) represents a polar structural element. In certain embodiments, the polar structural element is a macrocycle. Compounds 3 and 7 as shown in FIG. 10 are representative hydraphiles in which the polar element is not a macrocycle but rather a triethyleneoxy unit or an amide-containing module.

A more specific illustrative example of a lariat ether is the structure shown in Formula 3, where n has values from about 0 to about 16, or from about 4 to about 16, and $R^1$ is described below.

Formula 3

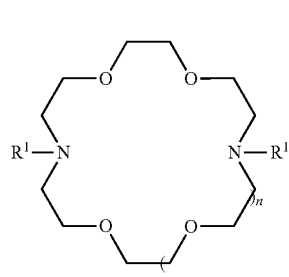

Lariat ethers similar to Formula 3 but having 12-membered macrocyclic rings are also provided for.

Figure 3:
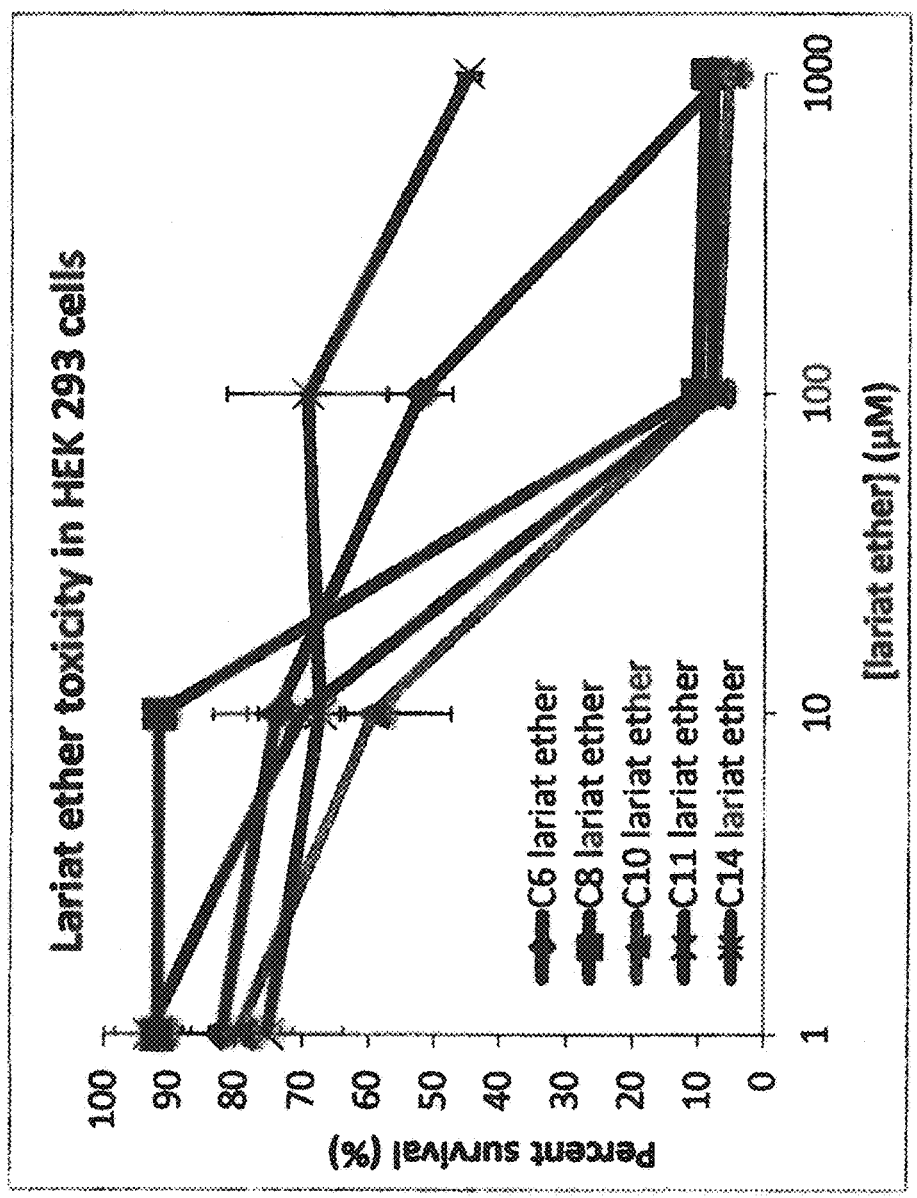
FIG. 3 is a graphical representation of lariat ether toxicity to HEK 293 cells.

The side arms ($R^1$) of lariat ethers can be linear or branched alkyl, unsaturated alkyl, aralkyl, or aryl, or heteroaryl. When the value of "n" in the structure of FIG. 3 is 1, the macrocyclic ring is 4,13-diaza-18-crown-6. When $R^1$ is saturated alkyl, the side chains can be methyl, ethyl, normal alkyl from n-propyl to n-eicosanyl (also called n-icosanyl) or branched chain isomers thereof. The corresponding branched chain isomers and/or unsaturated derivatives are also contemplated as are various ring sizes and heteroatom compositions including, but not limited to, O, N, and S. Non-limiting illustrative examples of lariat ethers include: diaza-18-crown-6 macrocycle with two linear alkyl chains ranging in length from 1 to 20 carbon atoms, or from 1 to 22 carbon atoms; diaza-15-crown-5 macrocycle with two linear alkyl chains ranging in length from 1 to 20 carbon atoms, or from 1 to 22 carbon atoms; N,N'-di-n-octyl-4,13-diaza-18-crown-6; N,N'-di-n-decyl-4,13-diaza-18-crown-6; N,N'-di-n-undecyl-4,13-diaza-18-crown-6; N,N'-di-n-dodecyl-4,13-diaza-18-crown-6; and N,N'-di-n-tetradecyl-4,13-diaza-18-crown-6. A representative example of a lariat ether having a more complex structure is the compound shown as 6 in FIG. 10. Compound 6 in FIG. 10 can also be described as a bolaamphiphile.

Formula 2 above shows a generalized structure for the compounds known as hydraphiles. In Formula 2, $R^2$ are the aforementioned side arms and the term "spacer" designates the linkage units that covalently connect the macrocyclic rings.

A more specific illustrative example of a hydraphile is the structure shown in Formula 4, where n is the number of methylene groups from 1-30.

Formula 4

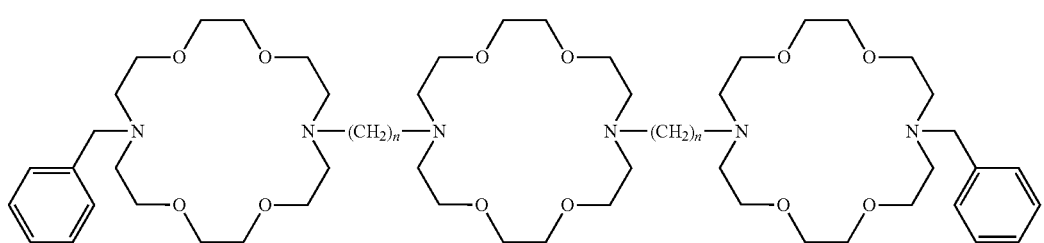

Some non-limiting illustrative examples of hydraphiles include: the structure of Formula 4:

Formula 4

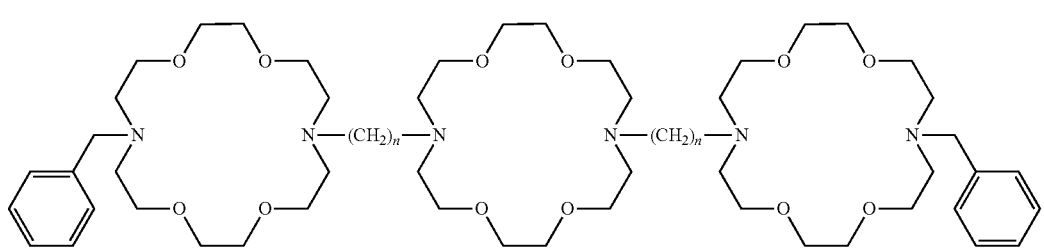

wherein n is 6; the structure of Formula 4:

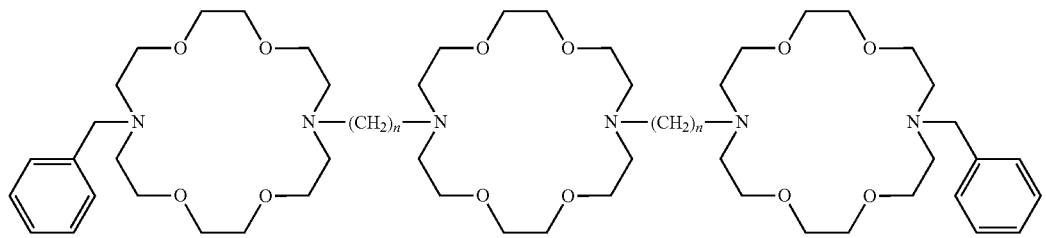

Formula 4 wherein n is 8; the structure of Formula 4:

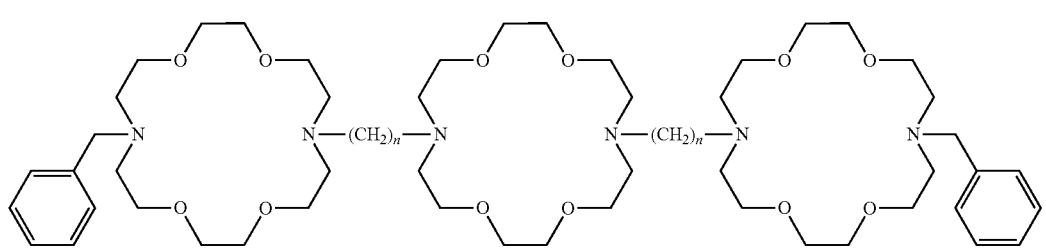

Formula 4 wherein n is 10, 12, 14, or 16; and the structure of Formula 2:

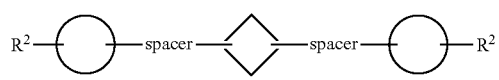

Formula 2 wherein the macrocycles (open circles) are 4,10-diaza-15-crown-5, the spacers are n-dodecylene, and the side chains ($R^2$) are n-dodecyl, and the diamond is 4,10-diaza-15-crown-5. Represented another way, in certain embodiments, the structure can be $R^2$—X—S—Y—S—X—$R^2$: wherein X (the macrocycles) can be 4,10-diaza-15-crown-5, S (spacers) can be n-dodecylene, $R^2$ (side chains) can be n-dodecyl, and Y (polar structural element) can be 4,10-diaza-15-crown-5.

Certain aspects are drawn to the administration of synthetic amphiphiles with antimicrobial agents. In certain embodiments, the synthetic amphiphile is a lariat ether or a hydraphile. A combination of the antimicrobial agent and the synthetic amphiphile can be administered by any route, protocol, means, etc., appropriate for its administration and embodiments are not limited to any particular route, protocol, means, etc. of administration. For example, the antibiotic and synthetic amphiphile can be administered to the microbe such as by contacting the microbe in culture or in solution or by applying the antibiotic and synthetic amphiphile to a material, such as the surface of a material, in or on which the microbe resides. Administration can be to a subject having a microbial infection and such administration to the subject results in administration to the microbe. For example, the subject can be a plant or an animal. In certain embodiments, the subject can be a mammal. In certain embodiments, the mammal subject can be a human having and suffering from a microbial infection. In certain embodiments, a combination of an antibiotic and a synthetic amphiphile as disclosed herein is administered in an effective amount. An "effective amount" is that amount, the administration of which to a subject (also referred to as a patient), either in a single dose or as part of a series, is effective for treatment. For example, and effective amount can be an amount that is sufficient to reduce the severity of a microbial infection (or one or more symptoms thereof), ameliorate one or more symptoms of an infection, prevent the advancement of the infection, cause regression of infection, or enhance or improve the therapeutic effect(s) of another therapy. In some embodiments, the effective amount cannot be specified in advance and can be determined by a caregiver, for example, by a physician or other healthcare provider, using various means, for example, dose titration. Appropriate therapeutically effective amounts can also be determined by routine experimentation using, for example, animal models.

In certain embodiments, the antimicrobial agent and the synthetic amphiphile can be administered orally, intravenously, intramuscularly, intraperitoneally, by ointment, cream or any other topical or surface application or surface coating. The antimicrobial agent and synthetic amphiphile can be administered in a single treatment or administered multiple times such as on a schedule or in a series over a period of time. The antimicrobial agent and the synthetic amphiphile can be administered at the same time or practically at the same time, such as immediate sequential administration. In certain embodiments, the antimicrobial agent and the synthetic amphiphile are pre-combined with each other into a composition comprising a combination of antimicrobial agent and synthetic amphiphile. Thus, the antimicrobial could be covalently attached to the hydraphile or lariat ether through an ester linkage which could be cleaved by endogenous esterase or amidase enzymes. In certain embodiments, the antimicrobial agent can be administered first followed by administration of the synthetic amphiphile. In certain embodiments, the synthetic amphiphile can be administered first followed by administration of the antimicrobial agent. The antimicrobial agent is considered to be administered with the synthetic amphiphile so long as both compositions are simultaneously contacted with a microbe even if not simultaneously applied, such as simultaneous in a culture with a microbe, simultaneously on a surface with a microbe, or simultaneously in a subject being treated. In certain embodiments, the simultaneous presence of both the antimicrobial agent and the synthetic amphiphile act together to enhance antimicrobial activity. In certain embodiments, the simultaneous presence of both the anti-microbial agent and the synthetic amphiphile reverse the resistance of a microbe to the anti-microbial agent.

In certain embodiments, the synthetic amphiphile, the antimicrobial agent, or both the synthetic amphiphile and the antimicrobial agent are administered at concentrations below their minimum inhibitory concentration (MIC) values. When certain antimicrobial agents and lariat ethers or certain antimicrobial agents and hydraphiles, one or more at concentrations below their minimum inhibitory concentrations, are co-administered to bacteria in the family Enterobacteriaceae (such as but not limited to E. coli), to bacteria in the family Bacillaceae (such as but not limited to B. subtilis), and to bacteria in the family Pseudomonadaceae (such as but not limited to Pseudomonas aeruginosa), the efficacy of the antibiotic/synthetic amphiphile combination is enhanced by as much as about 30-fold, or by as much as about 48-fold, or greater compared to the activity of either individual component. Efficacious results have been observed in the Gram negative bacterium Escherichia coli as the DH5α or K-12 strain. Other strains of E. coli are contemplated along with known strains of other Gram negative bacteria such as Pseudomonas aeruginosa. Application to Gram positive bacteria including but not limited to B. subtilis is also contemplated. Other bacteria and microbes, including but not limited to Candida albicans, Trichophyton rubrum, Aspergillus, Blastomyces dermatitides, Cryptococcus neoformans, Mycobacterium, Klebsiella, Enterococcus, Staphylococcus, and primitive eukaryotes such as yeast, for example Saccharomyces cerevisiae, and fungi, are also contemplated herein.

It has also been discovered that synthetic amphiphiles such as, but not limited to, lariat ethers and hydraphiles can be administered with an antimicrobial agent, such as an antibiotic, to organisms resistant to the antimicrobial agent, such that the resistant organism becomes susceptible to the antimicrobial agent. This is referred to herein as reversing the resistance of a microbe to an antimicrobial agent such as reversing the resistance of a bacterium to an antibiotic. As used herein, antibiotic "resistance" or the assertion that an organism is "resistant" to antibiotics means that some part or all of the organism in question does not respond to the antibiotic either by having its growth inhibited or being killed. For example, the tetracycline resistant E. coli reported herein were obtained by transformation of an E. coli purchased from a commercial supplier and it was found that their MIC was ~900 µM. This compares with the MIC of 12 µM reported in Table 5 for tetracycline against E. coli. This means that the tetracycline resistant E. coli requires a ~75-fold greater concentration of antibiotic to inhibit growth.

In certain embodiments, the synthetic amphiphile can be a bis(amide) compound having the chemical structure of Formula 5. The size of the macrocyclic ring can range from about 12 members to about 48 members. The side arms can be saturated or unsaturated alkyl, saturated or unsaturated aralkyl, aryl or substituted aryl including heteroaromatic groups. The side arms can possess heteroatoms such as oxygen, nitrogen, and/or sulfur. Heteroatoms can also be present in groups appended to the aryl or heteroaryl residues.

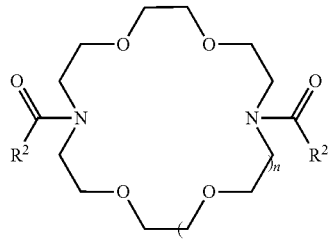

Formula 5

Figure 5:
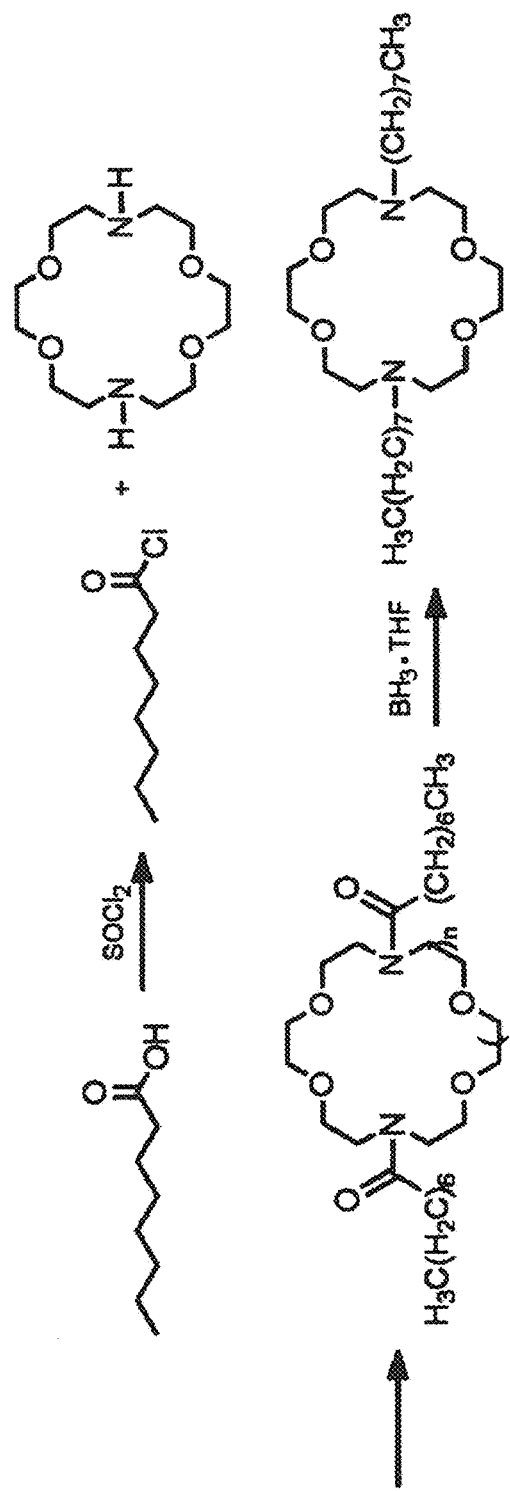
FIG. 5 is a synthetic scheme for the preparation of N,N'-di-n-octyl-4,13-diaza-18-crown-6.

The synthesis of compounds such as N,N'-bis(n-octyl)-4,13-diaza-18-crown-6 and N,N'-bis(n-undecyl)-4,13-diaza-18-crown-6 can readily be accomplished by methods known in the art. An example is to treat 4,13-diaza-18-crown-6 with an alkyl acid chloride such as n-octanoyl chloride, which in turn can be prepared from octanoic acid and a chlorinating agent such as thionyl chloride ($SOCl_2$) or oxalyl chloride (ClCOCOCl). The result of this reaction is a di-tertiary amide that can be reduced, for example, with lithium aluminum hydride ($LiAlH_4$) or borane ($BH_3.THF$). A typical reaction is illustrated in FIG. 5. It is meant to exemplify the synthetic approach and process but not to be in any way limiting.

Figure 13:
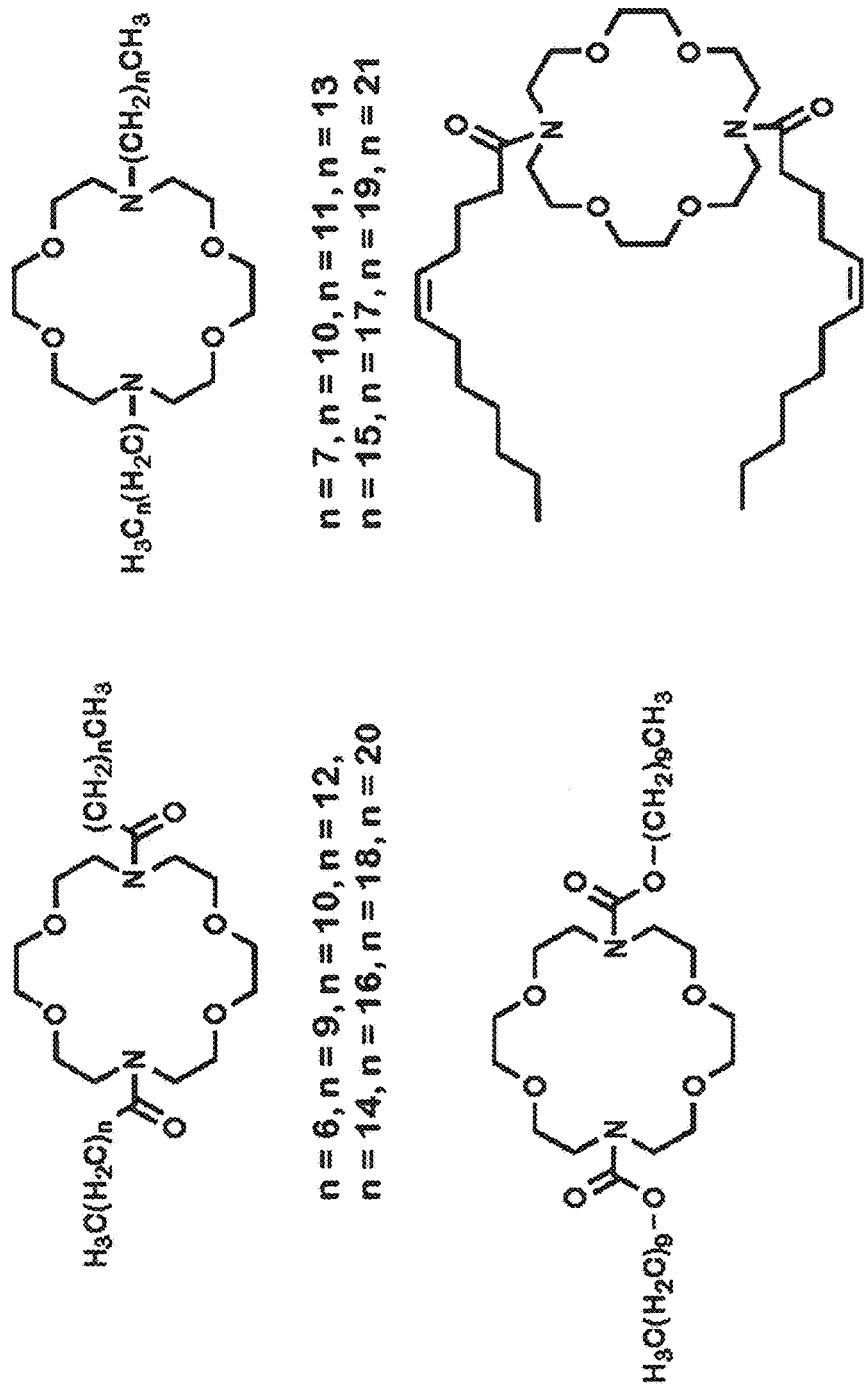
FIG. 13 shows illustrative examples of lariat ether structures that have been prepared.

In certain embodiments, lariat ether compounds can have ring sizes that range from 12 members to 48 members. The side chain substituents shown as $R^1$ or $R^2$ in Formulas 2 and/or 3, can be normal or branched alkyl having from 1-20 carbon atoms, or from 1-22 carbon atoms. These substituents can also be unsaturated, multiply unsaturated, cis and/or trans unsaturated, aralkyl, aromatic, or heteroaromatic. The side arms can possess heteroatoms such as oxygen, nitrogen, and/or sulfur. Heteroatoms can also be present in groups appended to the aryl or heteroaryl residues. Eighteen illustrative structures that have been prepared are shown in FIG. 13.

In certain embodiments, the microbe is E. coli, the antibiotic is selected from the group consisting of rifampicin, tetracycline, kanamycin, and erythromycin, and the synthetic amphiphile is N,N'-di-n-octyl-4,13-diaza-18-crown-6 or N,N'-di-n-undecyl-4,13-diaza-18-crown-6. In certain embodiments, the microbe is E. coli, the antibiotic is rifampicin, and the synthetic amphiphile is N,N'-di-n-octyl-4,13-diaza-18-crown-6. In certain embodiments, the microbe is E. coli, the antibiotic is tetracycline, and the synthetic amphiphile is N,N'-di-n-octyl-4,13-diaza-18-crown-6. In certain embodiments, the microbe is E. coli, the antibiotic is rifampicin, and the synthetic amphiphile is N,N'-di-n-undecyl-4,13-diaza-18-crown-6 lariat ether. In certain embodiments, the microbe is E. coli, the antibiotics is tetracycline, and the synthetic amphiphile is N,N'-di-n-undecyl-4,13-diaza-18-crown-6 lariat ether. In certain embodiments, the microbe is E. coli, the antibiotic is kanamycin, and the synthetic amphiphile is N,N'-di-n-undecyl-4,13-diaza-18-crown-6. In certain embodiments, the microbe is E. coli, the antibiotic is erythromycin, and the synthetic amphiphile is N,N'-di-n-undecyl-4,13-diaza-18-crown-6.

In certain embodiments, the microbe is a tetracycline resistant strain of E. coli, the antibiotic is tetracycline, and the synthetic amphiphile is a hydraphile. In certain embodiments, the microbe is a tetracycline resistant strain of E. coli, the antibiotic is tetracycline, and the synthetic amphiphile is benzyl $C_8$ hydraphile. In certain embodiments, the microbe is a tetracycline resistant strain of E. coli, the antibiotic is tetracycline, and the synthetic amphiphile is benzyl $C_{14}$ hydraphile.

Figure 14:
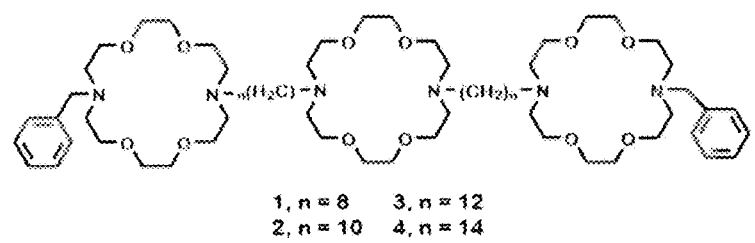
FIG. 14 shows structure of hydraphiles used for investigating mechanisms of antibiotic efficacy recovery. Hydraphiles consist of three diaza-18-crown-6 residues connected by alkyl spacer chains of appropriate length. The four hydraphiles used are $C_8$ hydraphile (1), $C_{10}$ hydraphile (2), $C_{12}$ hydraphile (3) and $C_{14}$ hydraphile (4).

To investigate the mechanism(s) of antibiotic efficacy recovery, a family of crown ether based synthetic ion channels/hydraphiles shown in FIG. 14 were developed and extensively studied. Since the resistance in Gram-negative bacteria is dependent on both efflux pumps and membrane permeability, it was hypothesized that the hydraphiles could overcome both of these barriers. Particularly, if amphiphiles, such as hydraphiles, could disrupt cation gradient and membrane integrity in bacteria, then the activity of efflux pumps could be decreased and that of antibiotics could be recovered. Since the membranes of each bacteria and mammalian cells have different composition, some selectivity was expected.

In this study, hydraphiles and other membrane disruptors are shown to significantly recover the efficacy of tetracycline, ciprofloxacin and norfloxacin against efflux pump expressing *E. coli, Klebsiella pneumoniae* and *Staphylococcus aureus* at sub-lethal concentrations. *E. coli* was unable to develop resistance to the hydraphiles. In the presence of the hydraphiles, the accumulation of substrate in the cell cytoplasm increased and the efflux pump activity decreased. A selective increase in the permeability of bacterial cells was also observed. At sub-lethal concentrations, the cytotoxicity to mammalian cells was minimal, and there was no increase in membrane permeability and the compound was bioavailable for up to 2 hours. There are no synthetic amphiphiles reported up to date that have recovered the activity of any antibiotics in the efflux pump expressing resistant bacteria. This study demonstrates, for the first time, that known membrane active amphiphiles can be used to recover the antimicrobial potency by potentially inhibiting the activity of efflux pumps in bacteria and selectively increasing permeability of bacterial cells.

In one embodiment, there is provided a method of inhibiting efflux pump activity in a multi-drug resistant bacterium. This method comprises administering to the bacterium with an amphiphile. In certain embodiments, the amphiphile is a compound comprising one or more polar head groups, and wherein each polar head group comprises at least three oxygen and hydrocarbon residues as the nonpolar elements.

In certain embodiments, the amphiphile is a synthetic amphiphile. The synthetic amphiphile can be a lariat ether or a hydraphile. In a preferred embodiment, the synthetic amphiphile is a hydraphile comprising the structure of Formula 4:

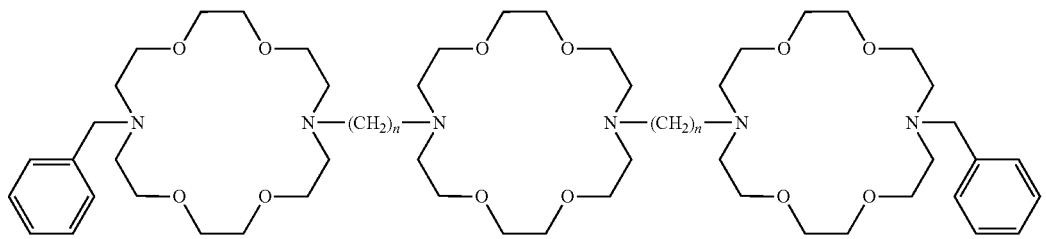

Formula 4 wherein n is 8, 10, 12, or 14.

In certain embodiments, the amphiphile is administered at a concentration below its minimum inhibitory concentration.

In certain embodiments, the amphiphile is administered as an aggregate or in a liposome.

In certain embodiments, the amphiphile is administered in a protonated or salt form.

In certain embodiments, the bacterium is a bacterium in the family Enterobacteriaceae, in the family Bacillaceae, or in the family Pseudomonadaceae. In a preferred embodiment, the bacterium is an efflux pump expressing Gram-positive or Gram-negative bacterium.

In another embodiment, there is provided a method of selectively increasing permeability of a bacterial cell. This method comprises administering to the bacterial cell with an amphiphile. In certain embodiment, the amphiphile is a compound comprising one or more polar head groups, and wherein each polar head group comprises at least three oxygen and hydrocarbon residues as the nonpolar elements.

In certain embodiments, the amphiphile is a synthetic amphiphile. The synthetic amphiphile can be a lariat ether or a hydraphile. In a preferred embodiment, the synthetic amphiphile is a hydraphile comprising the structure of Formula 4:

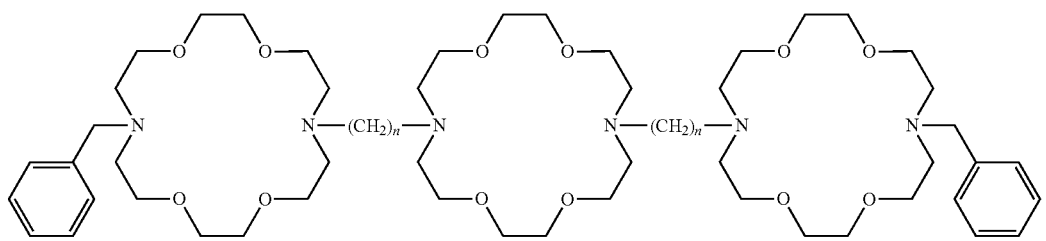

Formula 4 wherein n is 8, 10, 12, or 14.

In certain embodiments, the amphiphile is administered at a concentration below its minimum inhibitory concentration.

In certain embodiments, the amphiphile is administered as an aggregate or in a liposome.

In certain embodiments, the amphiphile is administered in a protonated or salt form.

In certain embodiments, the bacterium is a bacterium in the family Enterobacteriaceae, in the family Bacillaceae, or in the family Pseudomonadaceae. In a preferred embodiment, the bacterium is an efflux pump expressing Gram-positive or Gram-negative bacterium.

The following disclosed embodiments are merely representative. Thus, specific structural, functional, and procedural details disclosed in the following examples are not to be interpreted as limiting.

EXAMPLES

Among the organisms studied are several strains of the bacterium E. coli. These include, but are not limited to, DH5α, JM109, K-12, and tetracycline-resistant E. coli, the latter being an E. coli strain possessing the tet-A efflux pump. Experiments were conducted to determine the MIC values for the synthetic amphiphiles known as lariat ethers according to the procedures described in Antimicrobial M07-A9: *Methods for Dilution Antimicrobial Susceptibility Tests for Bacteria that Grow Aerobically*; Clinical and Laboratory Standards Institute, 2012; Vol. 32, 67 pp. MIC values so determined for several lariat ethers and for several antibiotics are shown in Table 1.

TABLE 1

Minimum Inhibitory Concentrations for Synthetic Amphiphiles and Antibiotics

| Antibiotic or $R^1$ in Formula 3 | MIC (µM) | | |
|---|---|---|---|
| | E. coli | B. subtilis | S. cerevisiae |
| n-octyl | 120 | 105 | 25 |
| n-decyl | 11 | 2.8 | 2.8 |
| n-undecyl | 24 | 9 | 1.5 |
| n-dodecyl | >300 | 2.5 | 2.5 |
| n-tetradecyl | >300 | >300 | >300 |
| n-hexadecyl | >300 | >300 | >300 |
| n-octadecyl | >300 | >300 | >300 |
| erythromycin | >400 | — | — |
| kanamycin | 30 | — | — |
| rifampicin | 60 | — | — |
| tetracycline | 12 | — | — |
| tobramycin | 15 | — | — |

Table 2 shows the effect of combining rifampicin or tetracycline with N,N'-bis(n-octyl)-4,13-diaza-18-crown-6 and then exposing the E. coli to the combination. Note that DMSO is the standard abbreviation for dimethylsulfoxide.

TABLE 2

Combination of $C_8$ lariat ethers and antibiotics against DH5α E. coli

| Side Chain | MIC (µM) | Used (µM) | Antibiotic | MIC (µM) | Used (µM) | vol-% DMSO | Fold Enhancement |
|---|---|---|---|---|---|---|---|
| n-$C_8$ | >120 | 80 | rifampicin | 64 | 3 ± 1 | 0.4 | 21 |
| n-$C_8$ | >120 | 60 | rifampicin | 64 | 3 ± 1 | 0.4 | 21 |
| n-$C_8$ | >120 | 40 | rifampicin | 64 | 3 ± 1 | 0.4 | 21 |
| n-$C_8$ | >120 | 100 | tetracycline | 12 | 0.25 | 0.4 | 48 |
| n-$C_8$ | >120 | 80 | tetracycline | 12 | 0.5 | 0.4 | 24 |
| n-$C_8$ | >120 | 60 | tetracycline | 12 | 2 | 0.4 | 6 |
| n-$C_8$ | >120 | 40 | tetracycline | 12 | 2 | 0.4 | 6 |
| n-$C_8$ | >120 | 30 | tetracycline | 12 | 3 | ≤0.6 | 4 |
| n-$C_8$ | >120 | 20 | tetracycline | 12 | 12 | 0.4 | 0 |

Table 2 also shows the effect of combining tetracycline with N,N'-bis(n-octyl)-4,13-diaza-18-crown-6 and then exposing the E. coli to the combination. The MIC of tetracycline decreases in the presence of DMSO.

Table 3 shows the effect of combining rifampicin or tetracycline with N,N'-bis(n-undecyl)-4,13-diaza-18-crown-6 and then exposing the E. coli to the combination.

TABLE 3

Combination of $C_{11}$ lariat ethers and antibiotics against DH5α E. coli

| Side Chain | MIC (µM) | Used (µM) | Antibiotic | MIC (µM) | Used (µM) | vol-% DMSO | Fold Enhancement |
|---|---|---|---|---|---|---|---|
| n-$C_{11}$ | 24 | 18 | rifampicin | 60 | 3 | 0.4 | 20 |
| n-$C_{11}$ | 24 | 16 | rifampicin | 60 | 6 | 0.4 | 10 |
| n-$C_{11}$ | 24 | 12 | rifampicin | 60 | 6 | 0.4 | 10 |
| n-$C_{11}$ | 24 | 8 | rifampicin | 60 | 15 | 0.4 | 4 |
| n-$C_{11}$ | 24 | 18 | tetracycline | 12 | 1.5 | 0.4 | 8 |
| n-$C_{11}$ | 24 | 16 | tetracycline | 12 | 0.25 | 0.4 | 48 |
| n-$C_{11}$ | 24 | 12 | tetracycline | 12 | 1 | 0.4 | 12 |
| n-$C_{11}$ | 24 | 4 | tetracycline | 12 | 3 | 0.4 | 4 |

Table 4 shows the effect on the K-12 strain of E. coli by combining various N,N'-disubstituted-4,13-diaza-18-crown-6 lariat ethers having side arms possessing six to twelve carbon atoms with either tetracycline or rifampicin.

TABLE 4

Combination of lariat ethers and antibiotics against K-12 E. coli

| Amphiphile | MIC (µM) | Used (µM) | Antibiotic | MIC (µM) | Used (µM) | Fold Enhancement |
|---|---|---|---|---|---|---|
| $C_8$ lariat ether | 300 | 64 | Tetracycline | 6 | 2.5 | ~2 |
| $C_{10}$ lariat ether | 12 | 1.5 | Tetracycline | 6 | 3 | 2 |
| $C_{11}$ lariat ether | 24 | 6 | Tetracycline | 6 | 2.5 | ~2 |
| $C_{12}$ lariat ether | >512 | 16 | Tetracycline | 6 | 3 | 2 |
| $C_6$ lariat ether | >512 | 250 | Rifampicin | 20 | 10 | 2 |
| $C_8$ lariat ether | 300 | 64 | Rifampicin | 20 | 5 | 4 |
| $C_8$ lariat ether | 300 | 32 | Rifampicin | 20 | 10 | 2 |
| $C_{10}$ lariat ether | 12 | 6 | Rifampicin | 20 | 5 | 4 |
| $C_{11}$ lariat ether | 24 | 6 | Rifampicin | 20 | 10 | 2 |

Previous studies of $C_{12}$ lariat ether did not show toxicity to DH5α E. coli cells but the compound was lethal to B. subtilis and to S. cerevisiae at minimum inhibitory concentrations (MICs) of 2.5 µM. The MICs of $C_6$, $C_8$, $C_{10}$, $C_{11}$, and $C_{14}$ lariat ether to DH5α E. coli were determined to be >360 µM, >240 µM, 12 µM, 24 µM and >360 µM respectively. Peak transport activity was observed for $C_{10}$ lariat ether, which was the most toxic compound in the MIC study. Two-armed $C_8$ and $C_H$ lariat ethers have also been shown to enhance the efficacy of rifampicin and tetracycline in DH5α E. coli. Here we have performed toxicity studies of lariat ethers to human embryonic kidney HEK-293 cells to determine the selectivity of the lariat ethers between mammalian and bacterial cells.

The toxicity of $C_6$, $C_8$, $C_{10}$, $C_{11}$ and $C_{14}$ lariat ethers to HEK-293 cells was determined by using an MTT assay. Results are presented in FIG. 3, in graphical form for the percent survival of HEK-293 cells in the presence of various concentrations of lariat ethers. The abscissa is a logarithmic scale for the concentrations ranging from 1 µM to 1000 µM (1 mM) used in the experiment. The ordinate represents percent survival of HEK-293 cells. For $C_8$ and $C_{11}$ lariat ether, concentrations equivalent to half MIC to E. coli, i.e. 60 µM and 12 respectively, were also tested for toxicity to HEK-293 cells.

FIG. 3 shows the percent survival of HEK-293 in the presence of various concentrations of lariat ethers. The ordinate ranges from 0-100% and records the survival of human embryonic kidney (HEK-293) cells when exposed to concentrations (1 µM to 1 mM) of lariat ethers having linear side arms ranging from six to fourteen carbon atoms.

As seen in FIG. 3, with the increase in concentrations of lariat ethers, the percent survival decreases. HEK-293 cells have 90% survival in the presence of 0.5% DMSO. Hence, the ~90% survival of HEK-293 cells in the presence of 1 µM $C_8$ and $C_{11}$ lariat ethers is attributed to the toxicity of DMSO (within experimental error as reflected in the error bars). $C_{14}$ lariat ether is considered non-toxic even at 1 mM (1000 µM) because 45% survival of HEK-293 is observed.

Figure 4:
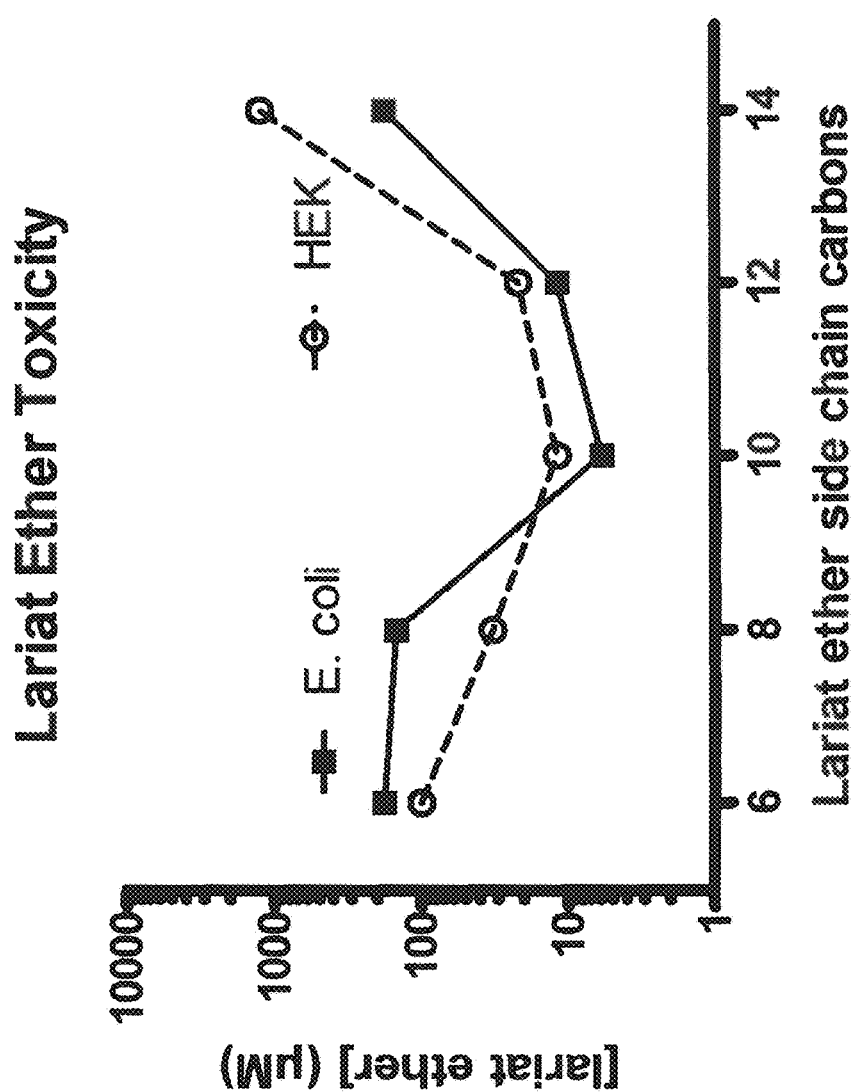
FIG. 4 is a graphical comparison of N,N'-dialkyl-4,13-diaza-18-crown-6 lariat ether toxicity ($LD_{50}$) to *E. coli* and to HEK 293 cells.

Two commonly used abbreviations are $LD_{50}$ and $IC_{50}$. The former is the concentration of an agent that comprises a lethal dose to 50% of the organism under study. The latter is the concentration of agent that inhibits growth of 50% of the organism under study. The data presented and graphed in FIG. 4 represent the averaged (multiple replicates) $LD_{50}$ concentrations of $C_6$, $C_8$, $C_{10}$, $C_{12}$, and $C_{14}$ lariat ethers against HEK-293 cells. It also shows the inhibitory concentration ($IC_{50}$) for each compound to DH5α $E.$ $coli$ cells. The abscissa represents the number of ($CH_2$) groups in spacer chains. The ordinate is logarithmic and reflects the concentrations (in µM) of the various lariat ethers used. The MIC values of $C_6$ and $C_{14}$ lariat ethers are greater than 360 µM but for the purpose of graphical presentation, the $IC_{50}$ values are considered at 180 µM. At 180 µM $C_6$ and $C_{14}$ lariat ethers are inactive against $E.$ $coli$.

FIG. 4 shows the toxicity of various side chain length lariat ethers to HEK-293 and DH5α $E.$ $coli$. In FIG. 4, the open circles (dashed line) represent the average $LD_{50}$ to HEK-293 cells whereas the squares (solid line) represent the $IC_{50}$ to $E.$ $coli$. The $IC_{50}$ for $C_8$ lariat ether to $E.$ $coli$ (150 µM) is much higher than the $LD_{50}$ to HEK-293 (33 µM). The $IC_{50}$ for $C_{11}$ lariat ether to $E.$ $coli$ (12 µM) is lower than the $LD_{50}$ to HEK-293 (22 µM). The synergy experiments for $C_8$ and $C_{ii}$ lariat ethers were performed at 60 µM and 12 µM, respectively. In the presence of 60 µM $C_8$ lariat ether, 27% survival of HEK-293 cells was observed. In the presence of 12 µM $C_{ii}$ lariat ether, 66% survival of HEK-293 cells was observed. With the increase in side chain length of lariat ethers, the $IC_{50}$ to $E.$ $coli$ is observed to be lower than $LD_{50}$ to HEK-293. This data suggests that with an increase in side chain length, the toxicity of lariat ether to HEK-293 is lower than that to $E.$ $coli$. Similar to the toxicity trend in $E.$ $coli$, $C_{10}$ lariat ether had the highest toxicity to HEK-293.

Minimum inhibitory concentrations were determined using protocols described above for various synthetic amphiphiles and antimicrobials against DH5α, K-12, and tetracycline-resistant strains of $E.$ $coli$. The data are summarized in Table 5. N,N'-Dibenzyl-4,13-diaza-18-crown-6 is referred to in the table as dibenzyldiaza-18-crown-6. The compounds referred to as $C_8$ benzyl hydraphile and $C_{14}$ benzyl hydraphile have the structures shown in Formula 4, in which "n" is 8 and 14, respectively.

Initial studies of hydraphile-enhanced antimicrobial activity were conducted with three hydraphiles. These are illustrated in Formula 4, in which "n"=12, 14, and 16. In several published studies, it was found that hydraphiles having spacer chains [—($CH_2$)$_n$—] in the 12-16 range were invariably the most active ion transporters. These results can be found in the following articles: *Chemical Communications* 1998, 2477-2478 and *Journal of Supramoleular Chemistry* 2001, 1, 23-30. It was discovered that hydraphiles that successfully formed ion channels in membranes also killed $E.$ $coli$, as reported in the *Journal of the American Chemical Society* 2002, 124, 9022-9023. In this report, the hydraphile having —($CH_2$)$_8$— spacers did not exhibit toxicity to $E.$ $coli$, whereas the benzyl $C_{12}$ hydraphile having —($CH_2$)$_{12}$— spacers killed the bacteria.

All previous studies, both biophysical and biological, indicated that hydraphiles of the general type shown in Formula 4 would be inactive on their own or as adjuncts to antimicrobial agents if their spacer chains [—($CH_2$)$_n$—] contained 8 or fewer methylene groups. It was unexpectedly discovered that the short hydraphile benzyl $C_8$ significantly enhanced the potency of several antibiotics.

Studies with a tetracycline-resistant strain of $E.$ $coli$, specifically tetracycline-resistant JM109, have shown that lariat ethers produce significant enhancements of antimicrobial potency. A JM109 strain that is highly resistant to the antibiotic tetracycline was studied in the presence of various lariat ethers at different concentrations. As shown by the data in Table 6, the antimicrobial resistance was reversed. Table 5 shows the results for the tetracycline-resistant JM109 strain of $E.$ $coli$ in the presence of lariat ethers.

TABLE 5

MIC values for synthetic amphiphiles or antimicrobials against tetracycline resistant $E.$ $coli$

| Amphiphile | Antimicrobial | MIC (µM) |
|---|---|---|
| $C_8$ hydraphile | None | 250 ± 10 |
| $C_{10}$ hydraphile | None | 35 ± 5 |
| $C_{12}$ hydraphile | None | 5 ± 0.5 |
| $C_{14}$ hydraphile | None | 2 ± 0.125 |
| $C_6$ lariat ether | None | >512 |
| $C_8$ lariat ether | None | 120 |
| $C_{10}$ lariat ether | None | 16 |
| $C_{11}$ lariat ether | None | 24 |
| $C_{12}$ lariat ether | None | >512 |
| None | Tetracycline | 900 ± 50 |
| None | Ampicillin | >1000 |

Studies with several strains of $E.$ $coli$ have shown that lariat ethers produce significant enhancements of antimicrobial potency. In particular, a study of tetracycline-resistant $E.$ $coli$ showed that in the presence of lariat ethers, the antimicrobial resistance was reversed. Data are shown in Table 6 for treatment with lariat ethers and tetracycline of tetracycline-resistant strains of $E.$ $coli$.

TABLE 6

Combination of lariat ether and tetracycline against tetracycline resistant $E.$ $coli$

| Amphiphile | MIC (µM) | Used (µM) | Antibiotic | MIC (µM) | Used (µM) | Fold Enhancement |
|---|---|---|---|---|---|---|
| $C_6$ lariat ether | >512 | 192 | Tetracycline | 900 | 413 | 2 |
| $C_8$ lariat ether | 120 | 80 | Tetracycline | 900 | 87 | 10 |
| $C_8$ lariat ether | 120 | 60 | Tetracycline | 900 | 175 | 5 |
| $C_8$ lariat ether | 120 | 40 | Tetracycline | 900 | 233 | 4 |
| $C_{10}$ lariat ether | 16 | 6 | Tetracycline | 900 | 225 | 4 |
| $C_{10}$ lariat ether | 16 | 9 | Tetracycline | 900 | 56 | 16 |
| $C_{11}$ lariat ether | 24 | 18 | Tetracycline | 900 | 87 | 10 |
| $C_{11}$ lariat ether | 24 | 16 | Tetracycline | 900 | 87 | 10 |
| $C_{11}$ lariat ether | 24 | 12 | Tetracycline | 900 | 87 | 10 |
| $C_{11}$ lariat ether | 24 | 8 | Tetracycline | 900 | 175 | 5 |
| $C_{12}$ lariat ether | >512 | 192 | Tetracycline | 900 | 450 | 2 |

Studies with several strains of $E.$ $coli$ have shown that hydraphiles produce significant enhancements of antimicrobial potency. In particular, a study of tetracycline-resistant $E.$ $coli$ showed that in the presence of hydraphiles, the antimicrobial resistance was reversed. Data are shown in Table 7 for treatment with hydraphiles and tetracycline of tetracycline-resistant strains of $E.$ $coli$.

TABLE 7

Combination of hydraphile and tetracycline against tetracycline resistant *E. coli*

| Amphiphile | MIC (μM) | Used (μM) | Antibiotic | MIC (μM) | Used (μM) | Fold Enhancement |
|---|---|---|---|---|---|---|
| $C_8$ hydraphile | 250 | 125 | Tetracycline | 900 | 30 | 30 |
| $C_8$ hydraphile | 250 | 62.5 | Tetracycline | 900 | 82 | 11 |
| $C_{10}$ hydraphile | 35 | 17.5 | Tetracycline | 900 | 40 | 23 |
| $C_{10}$ hydraphile | 35 | 8.75 | Tetracycline | 900 | 200 | 5 |
| $C_{12}$ hydraphile | 5 | 2.5 | Tetracycline | 900 | 55 | 16 |
| $C_{12}$ hydraphile | 5 | 1.25 | Tetracycline | 900 | 400 | 2 |
| $C_{14}$ hydraphile | 2 | 1 | Tetracycline | 900 | 220 | 4 |
| $C_{14}$ hydraphile | 2 | 0.5 | Tetracycline | 900 | 360 | 3 |

The synthetic amphiphile shown as Compound 6 in FIG. 10 was examined with two *E. coli* strains: K-12 and the tetracycline resistant strain. In the presence of tetracycline and in the absence of a synthetic amphiphile, the MIC values against K-12 and the tetracycline resistant strain were 6 μM and 900 μM, respectively. For the K-12 strain, addition of Compound 6 in FIG. 10 at a concentration of approximately half its MIC, in the presence of tetracycline, altered the MIC of tetracycline from 6 μM to 2 μM. This is an approximately three-fold increase in efficacy. For the tetracycline-resistant strain, addition of compound 6 in FIG. 10 at a concentration of approximately half its MIC, in the presence of tetracycline, altered the MIC of tetracycline from 900 μM to 150 μM. This is an approximately six-fold increase in efficacy.

Figure 6:
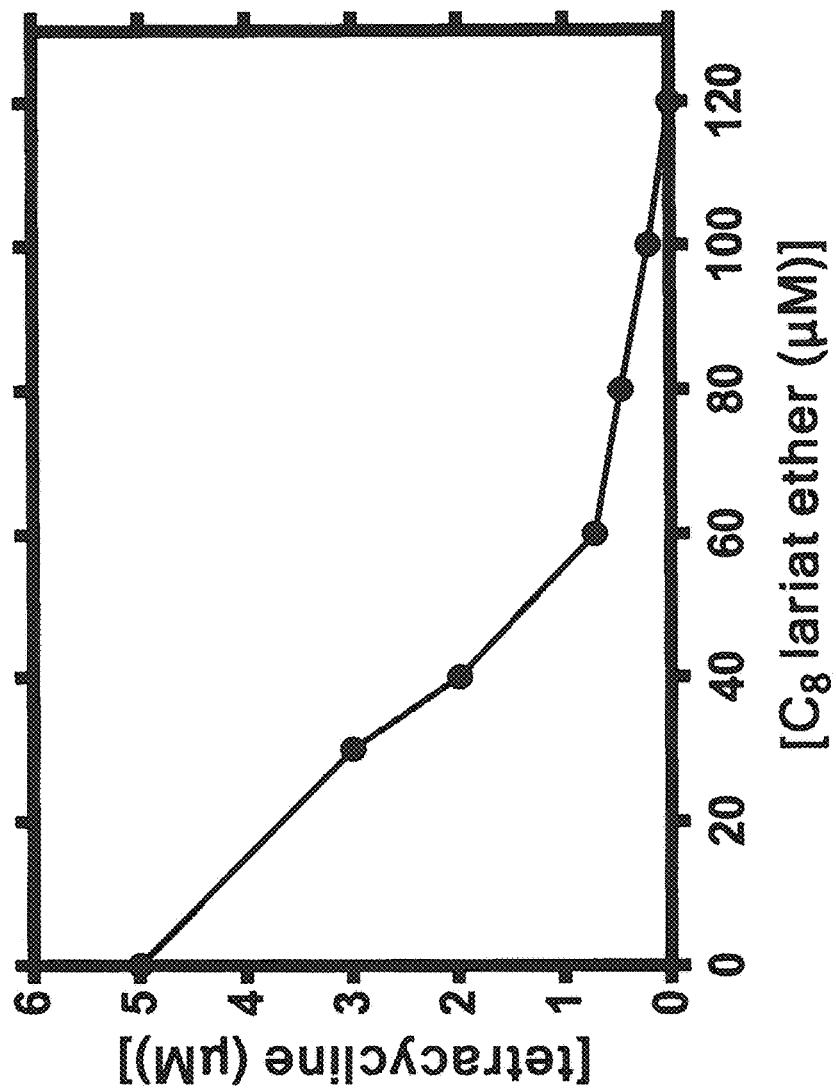
FIG. 6 is a graph showing the relationship between the concentrations of synthetic amphiphile and antibiotic required to inhibit the growth of DH5α *E. coli* treated with $C_8$ lariat ether and tetracycline.
Figure 7:
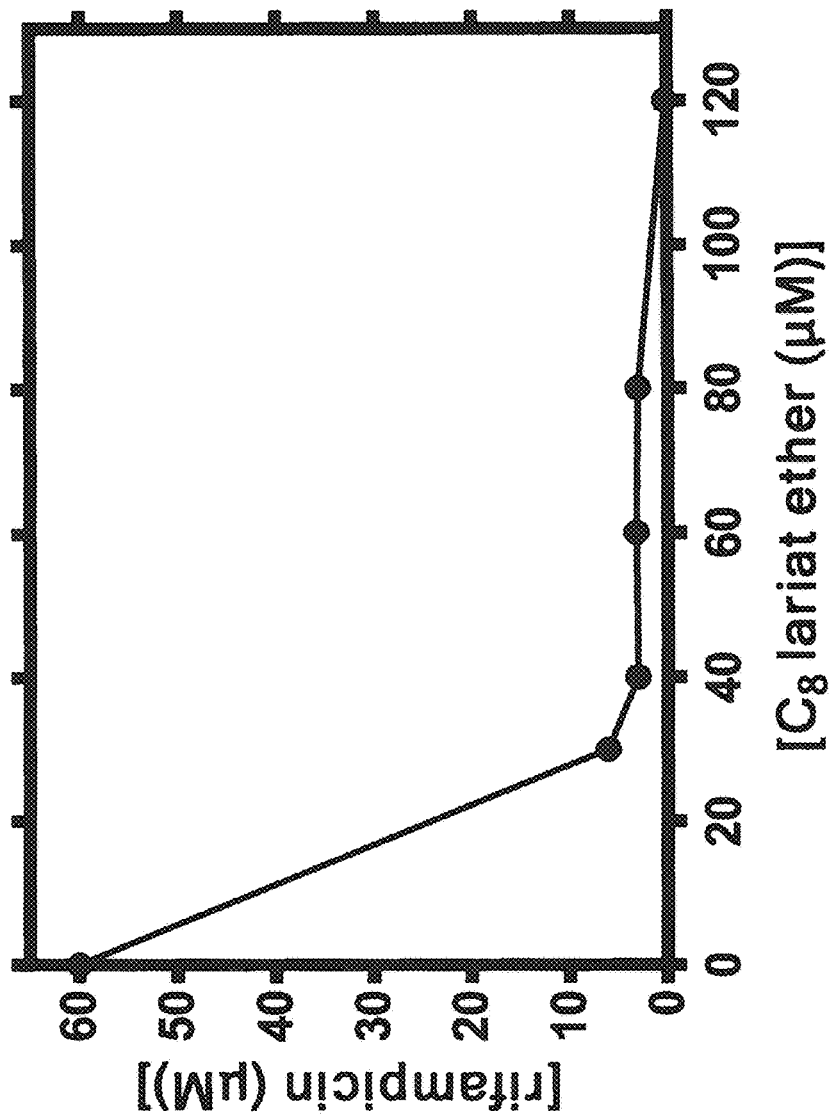
FIG. 7 shows the minimum inhibitory concentration (MIC) for DH5α *E. coli* treated with $C_8$ lariat ether and rifampicin when treated with various concentrations of amphiphile and antibiotic.
Figure 8:
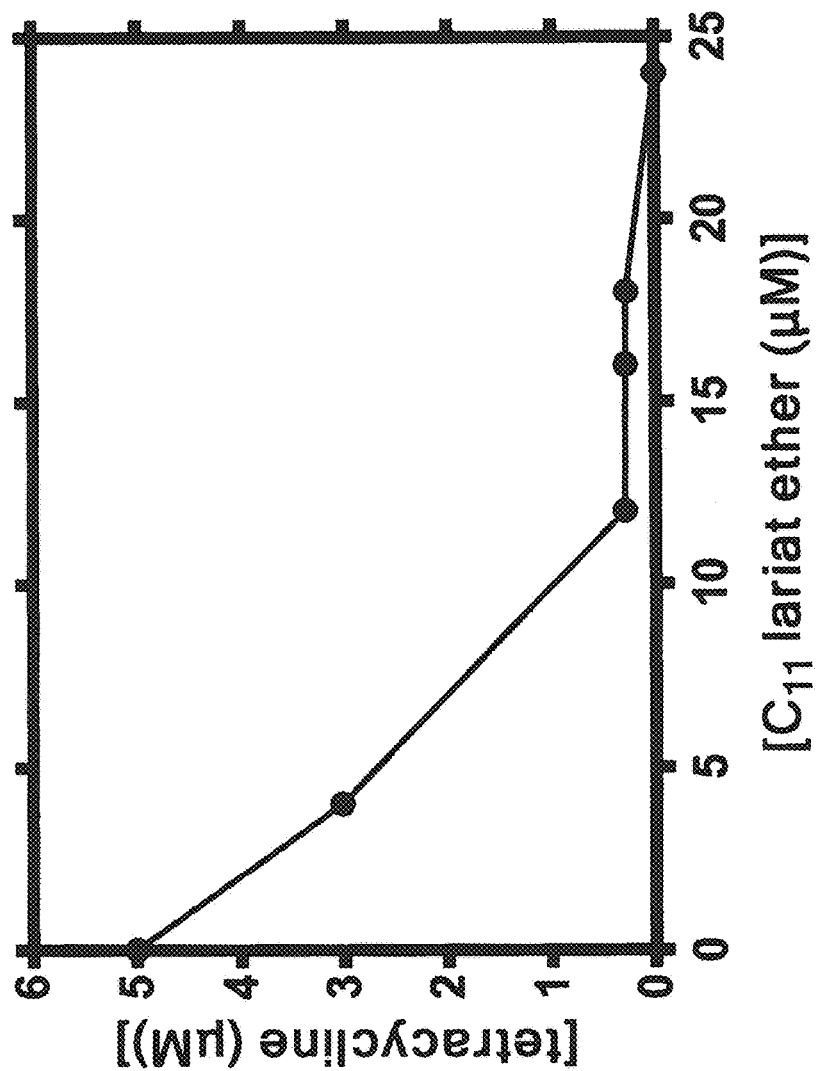
FIG. 8 shows the minimum inhibitory concentration (MIC) for DH5α *E. coli* treated with $C_{11}$ lariat ether and tetracycline when treated with various concentrations of synthetic amphiphile and antibiotic.
Figure 9:
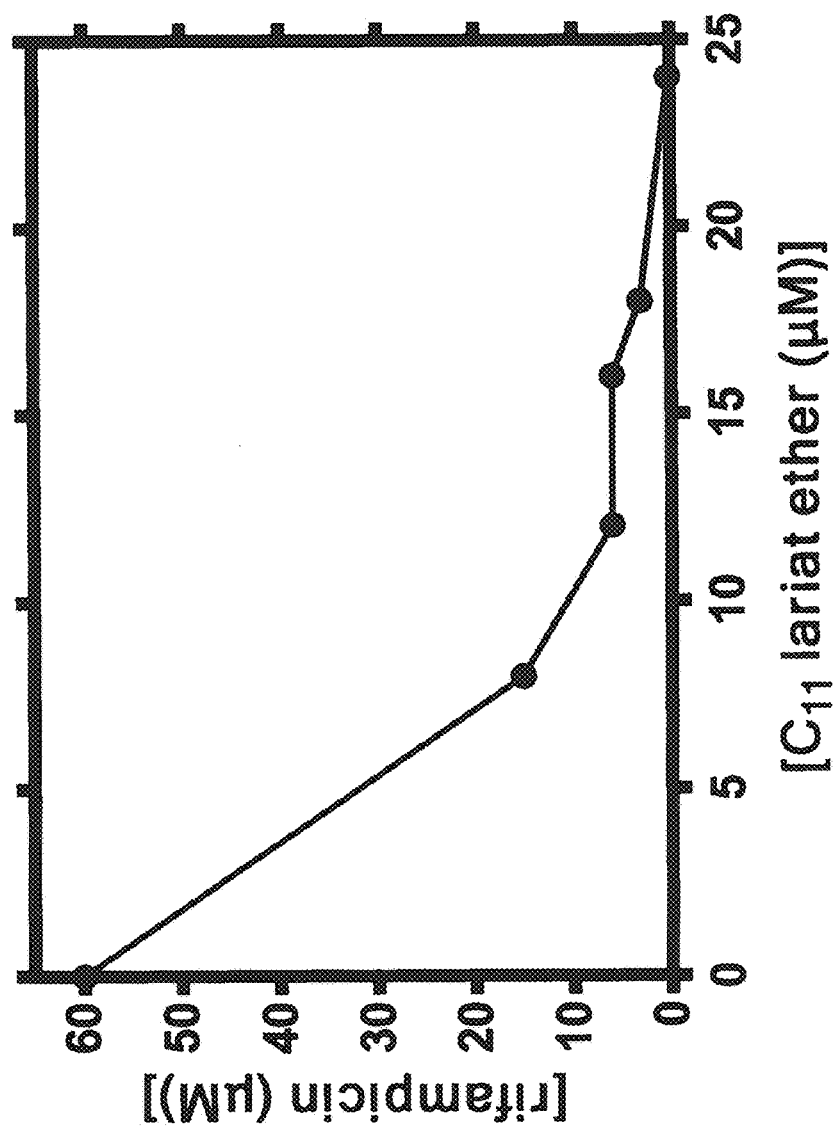
FIG. 9 shows the minimum inhibitory concentration (MIC) for DH5α *E. coli* treated with $C_{11}$ lariat ether and rifampicin when treated with various concentrations of synthetic amphiphile and antibiotic.

Referring to FIGS. 6 through 9 which show plots of antibiotic concentration as a function of lariat ether concentration for the antibiotics tetracycline and rifampicin with $C_8$ and $C_{11}$ lariat ethers. FIG. 6 is a graph showing the relationship between the concentrations of synthetic amphiphile and antibiotic required to inhibit the growth of *E. coli* treated with $C_8$ lariat ether and tetracycline. FIG. 7 is a graph showing the relationship between the concentrations of synthetic amphiphile and antibiotic required to inhibit the growth of *E. coli* treated with $C_8$ lariat ether and rifampicin. FIG. 8 is a graph showing the relationship between the concentrations of synthetic amphiphile and antibiotic required to inhibit the growth of for *E. coli* treated with $C_{11}$ lariat ether and tetracycline. FIG. 9 is a graph showing the relationship between the concentrations of synthetic amphiphile and antibiotic required to inhibit the growth of *E. coli* treated with $C_{11}$ lariat ether and rifampicin. Graphical representations are known to those in the art as a means to assess whether a combination of drugs is additive or synergistic as described in *Drug Synergism and Dose-Effect Data Analysis*; Chapman & Hall: Boca Raton, 2000, 267 pp.

Hydraphiles and other synthetic amphiphiles have been known for decades. The majority of the studies with these molecules have been focused on the development of new structures and their effect on ion transport. Many studies have also reported their activity as antibiotics, which is greater against Gram-positive bacteria. The present study reports for the first time that synthetic amphiphiles could be used to recover the efficacy of antibiotics against efflux pump expressing and multi drug resistant bacteria or 'Superbugs'. The study as illustrated in the examples below show that hydraphiles could recover the activity of tetracyclines and fluoroquinolones against two Gram negative and one Gram positive bacteria. One of these bacteria is *K. pneumoniae*, which was isolated from a patient, and is an urgent threat to public health. This bacterium is resistant to almost all known classes of antibiotics and the last resort of treatment is Colistin. However, Colistin does have cytotoxicity issues. Recovery of antimicrobial efficacy by hydraphiles could make this infection treatable.

As seen in the following examples, hydraphiles could inhibit the activity of efflux pumps and increase the accumulation of substrate (antibiotics) in the cell cytoplasm. This efflux pump inhibition by hydraphiles is indirect as observed with CCCP rather than direct inhibition as observed with PAβN or reserpine. One advantage of such an approach is that bacteria cannot easily develop resistance to amphiphiles that transport ions and disrupt membranes. A single mutation in the amino acid chain of an efflux pump peptide can render molecules such as reserpine and PAβN useless. It is shown here that *E. coli* cannot develop resistance to hydraphiles for over 15 days.

The inhibition of efflux pumps by hydraphiles is caused by disruption of ion gradients and/or membrane integrity. However, this raises the issue of cytotoxicity and bioavailability. Preliminary results show that hydraphiles were bioavailable through IV for over 2 hours. Cytotoxicity of hydraphiles at sub-MIC concentrations was minimal.

Overall, disclosed herein is a non-resistant adjuvant platform that could be used with novel molecules to recover antimicrobial potency against life-threatening bacterial infections.

Example 1: N,N'-Di-n-octyl-4,13-diaza-18-crown-6

This compound was prepared by methods known in the art. 4,13-Diaza-18-crown-6 was acylated with octanoyl chloride and the resulting diamide was reduced with $B_2H_6$.THF. Short path distillation afforded the lariat ether (63%) as a colorless oil (bp 181-190° C., 0.04 torr).

Example 2: Determination of Minimum Inhibitory Concentrations (MIC)

Minimal Inhibitory Concentration (MIC) Procedure. The steps used in the experimental determination of the minimum inhibitory concentration (MIC) are recorded below.

1. Streak the *E. coli* (DH5α or K-12 MG1655) strain on L.B agar plates. For tetracycline resistant *E. coli* use L.B. agar+ampicillin plates (150 μM).
2. Inoculate a 2 mL of L.B. Miller media with one colony of bacteria and incubate overnight at 37° C. and 200 rpm. For tetracycline resistant *E. coli*, use 128 μM ampicillin in L. B. Miller media.
3. Prepare an excel file outlining the concentrations and volumes of compound and L.B. Miller media required to be added to each test tube. Note: The total volume of media is 2000 μL in each test tube.
4. Prepare initial concentration of all the compounds required.
5. Dilute from the initial concentration according to the required concentration of the compound. Note: For compounds that are dissolved in DMSO, dilutions must be made in a way that the volume of DMSO added to each test tube is kept constant at 5 μL (0.25% by volume). For compounds that are dissolved in water, the volume of water added to media is constant at 5 (0.25% by volume).
6. Add the appropriate volume of media to each test tube.
7. In a separate test tube, knock back *E. coli* to optical density (λ=600 nm, O.D.)=0.100 by adding 50 μL of *E. coli* to 1950 μL of L.B. Miller media. Check O.D. every 30 minutes until the *E. coli* grows to O.D.=0.600.
8. While the *E. coli* grows, add the appropriate volume of compound to each test tube. Vortex each test tube for 2-3 seconds.

9. Add 20 µL E. coli grown to O.D.=0.600 to each sample. Note: Manage experiments so that E. coli is grown to O.D.=0.600 before adding to each test tube.
10. Vortex each test tube for 2-3 seconds.
11. Inoculate test tubes at 37° C. and 200 RPM for 24 hours. Results are determined by visual verification or O.D. ($\lambda$=600 nm) measurement of the growth or no growth of bacteria.

Example 3: Tetracycline Efficacy Recovery Study with N,N'-Di-n-Octyl-4,13-Diaza-18-Crown-6

This study was conducted with N,N'-di-n-octyl-4,13-diaza-18-crown-6 ($C_8$ lariat ether). A stock solution was prepared at a concentration of 20 mM in DMSO. A tetracycline stock solution was prepared at a concentration of 1 mM in Milli-Q $H_2O$. An 80 µM solution of $C_8$ lariat in media was prepared by adding 8 µL of $C_8$ lariat stock solution (20 mM) to 2 mL media. Preparation of 60 µM, 40 µM, and 20 µM solutions of $C_8$ lariat, 6 µL, 4 µL, and 2 µL of $C_8$ lariat stock solution (20 mM) was added to 2 mL media respectively and to make the volume of DMSO the same (0.4 vol-% with respect to media) appropriate volume of DMSO was added (2, 4, and 6 of µL DMSO respectively).

Example 4: Co-Administration of Antibiotics and Lariat Ethers to E. coli. $C_8$ Lariat (MIC=120 µM) and Tetracycline Against E. coli DH5α (MIC=10 µM)

Each concentration of $C_8$-lariat was tested with different concentrations of tetracycline (from 6 µM to 0.25 Tetracycline was dissolved in water. The volume of water added was between 12 to 0.5 µL. The volume of water added was not constant but the volume of media was changed so that the total volume was kept constant at 2 mL.

Example 5: Procedure for Assessment of Potential Antibiotic Synergy

1. Steps 1-7, described in the MIC procedure, shown in Example 2, were followed.
2. While the E. coli grew, the appropriate volume of compound was added to each test tube.
3. Antibiotics were added at the required volume of solution to obtain the desired concentration in each test tube. The concentration of each compound was adjusted so that the total volume of DMSO added to each test tube was 5 µL (0.25% by volume with respect to final volume i.e. 2000 i.e. 2 mL).
4. Each test tube was vortexed for 2-3 seconds.
5. Steps 10-12 from the MIC procedure, shown in Example 2, were then executed.

Example 6: Determination of Toxicity of Lariat Ethers to HEK-293 and E. coli Cells Growth medium containing DMEM with high glucose (ATCC), 10% fetal bovine serum (FBS; Sigma-Aldrich) and 10 µg/mL of blasticidin (Thermo-Fischer) was prepared. HEK 293 cells were thawed out from cryo-preserved samples in 10 mL growth media, centrifuged at 500 rpm for 10 minutes to remove preservative. The cells were then resuspended in fresh growth medium and cultured using a T-75 flask (Thermo-Fischer) at 37° C. and 5% $CO_2$. Cells were monitored for confluence and growth medium was replaced every 48 h, until cells were placed onto a 96-well plate for toxicity studies.

After reaching 80-90% confluence, cells were trypsinized and suspended in media containing DMEM and 10% FBS (no antibiotics). The cells were counted on a hemacytometer and plated at a density of 20,000 cells per well in a 96-well plate and grown for 24 hours to reach 60-70% confluence. DMSO stocks of $C_6$, $C_8$, $C_{10}$, $C_{11}$ and $C_{14}$ diaza-18-crown-6 lariat ethers were prepared at 200 mM and diluted 1:10 to get working concentrations of 20 mM, 2 mM, and 0.2 mM. Each stock solution was further diluted 1:100 into DMEM supplemented with 10% FBS to get final concentrations of 1 mM, 0.1 mM, 0.01 mM (10 µM) and 0.001 mM (1 The original media was then removed from the cells and replaced with 200 µL media containing the desired concentration of compound. Three wells were used for each concentration providing experimental triplicates. As a positive control for growth, three wells containing cells were treated with DMEM supplemented with 10% FBS. For DMSO control, three wells containing cells were treated with DMEM supplemented with 10% FBS and 0.5% DMSO. As a negative control, wells without cells were treated with DMEM supplemented with 10% FBS and 0.5% DMSO. The 96-well plate was then returned to 37° C. and 5% $CO_2$ for 24 hours. After incubation, MTT assay (Sigma-Aldrich) was performed according to manufacturer's protocol. The absorbance was measured at 570 nm and nonspecific absorbance was corrected at 650 nm, using SpectraMax340 micro plate reader.

The experiment was performed in triplicate and the average of percent survival of three experiments was determined. The graph in FIG. 3 represents the percent survival with increasing concentration of lariat ethers on a logarithmic scale. The error bars represent the standard error. The lethal dose 50 ($LD_{50}$) for each compound was calculated by using the equation for a logarithmic regression curve. The $R^2$ value for each curve was approximately 0.9.

Example 7: Compounds and Bacteria Used in Mechanism Study

This study involved the use of $C_8$, $C_{10}$, $C_{12}$ and $C_{14}$ hydraphiles (compounds 1-4 as shown in FIG. 14). All the hydraphiles have two distal benzyl groups. Antibiotics tetracycline and ciprofloxacin were used in this study. Gramicidin D, valinomycin and Triton X-100 were used as controls to compare the activity of the above hydraphiles to that of known protein ion channel, a protein ion carrier, or simply a detergent. Known efflux pump inhibitors such as reserpine and CCCP were also used. All the antibiotics and controls were acquired from Sigma-Aldrich and were used as received.

To test the hypothesis that the hydraphiles could overcome the efflux pumps and membrane permeability barriers in Gram-negative bacteria, a strain of Escherichia coli resistant to tetracycline and ampicillin ($Tet^R$ E. coli) was developed. Tetracycline resistance in $Tet^R$ E. coli is caused by the tetA [class C] gene that encodes a tetracycline specific efflux pump (tetA) spanning the cytoplasmic membrane (Sapunaric and Levy; Substitutions in the interdomain loop of the Tn10 TetA efflux transporter alter tetracycline resistance and substrate specificity, *Microbiol.* 2005, 151, 2315-2322; Thanassi, et al., Role of outer membrane barrier on efflux-mediated tetracycline resistance of Escherichia coli. *J. Bacteriol.*, 1995, 177, 998-1007). K. pneumoniae (ATCC BAA 2146; another Gram-negative bacterium) that expresses multiple classes of efflux pumps and NDM-1 gene was also used. This *K. pneumoniae* is a clinically relevant strain that was isolated from a patient. Gram-positive *S. aureus* 1199B was used that overexpresses the NorA efflux pump. Since ethidium bromide and norfloxacin are the substrates of efflux pumps, *S. aureus* 1199B was used to evaluate the activity of efflux pumps in the presence of the hydraphiles and other membrane disruptors.

Example 8: Antimicrobial Activity

The minimal inhibitory concentrations (MIC) of all the compounds against three bacterial strains were first determined using the microtiter technique as described above. Inhibition greater than 80% was considered as the MIC (Table 8). $C_{14}$ and $C_{12}$ hydraphiles that could span the bilayer showed the lowest MICs, whereas $C_{10}$ and $C_8$ hydraphiles were less active as antimicrobials. All four hydraphiles were more active against Gram-positive bacteria. The MIC of $C_{14}$ hydraphile against *E. coli* was 2 µM and against *S. aureus* at 1 µM. The MIC of $C_{12}$ hydraphile was lowest against *S. aureus* at 0.5 µM. $C_{14}$ hydraphile had a MIC of 10 µM against *K. pneumoniae* that was reported to be resistant to 34 different antibiotics. Antimicrobial property of hydraphiles is attributed to the disruption of ion homeostasis in bacteria. MICs of antibiotics against all three strains were as expected. $Tet^R$ *E. coli* was resistant to tetracycline (900 µM) and Ampicillin (>1000 µM) but sensitive to other antibiotics tested (Table 9). *S. aureus* 1199B was resistant to ethidium bromide (MIC), norfloxacin and ciprofloxacin (MIC) but sensitive to others.

TABLE 8

Minimal Inhibitory Concentrations (MIC)

| Compounds used | *K. pneumoniae* | *E. coli* ($Tet^R$) | *S. aureus* 1199B |
|---|---|---|---|
| $C_8$ hydraphile | 200 | 250 | 128 |
| $C_{10}$ hydraphile | 56 | 35 | 8 |
| $C_{12}$ hydraphile | 35 | 5 | 0.5 |
| $C_{14}$ hydraphile | 10 | 2 | 1 |
| Tetracycline | 1000 | 900 | N.D. |
| Ciprofloxacin | 700 | 0.5 | N.D. |
| CCCP | N.D. | 56 | ≤4 |
| Reserpine | N.D. | >128 | >128 |

N.D.—Not determined

Example 9: Combination Studies

Hydraphiles have been shown to transport ions through liposomes and mammalian cells and inhibit bacterial growth. However, the bacterial strains used herein are multidrug resistant and the effect of hydraphiles on the inhibition of resistance mechanism (efflux pumps) was not known. The hydraphiles and the controls were tested next to see whether they could recover the activity of antibiotics against efflux pump expressing Gram-positive and Gram-negative bacteria. The MIC of antibiotics were determined in the presence of ½ [MIC] or ¼ [MIC] of each hydraphile or the controls used.

Figure 15B:
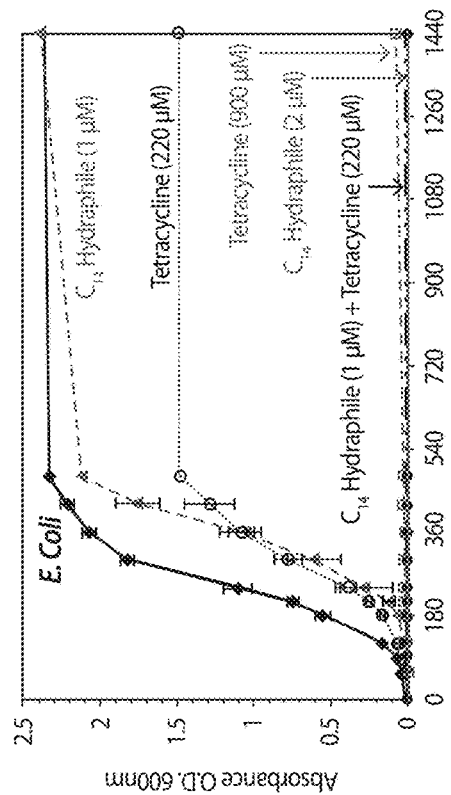
FIG. 15B shows cytotoxicity of $C_8$-$C_{14}$ hydraphiles at MIC concentration to HEK-293, Cos-7 and HeLa cells.

The results show that at ½ [MIC] and ¼ [MIC] of $C_8$-$C_{14}$ hydraphiles, the activity of tetracycline against $Tet^R$ *E. coli* was recovered. At ½ [MIC], $C_8$ hydraphile recovered the activity of tetracycline by 30-fold, $C_{10}$ hydraphile by 23-fold, $C_{12}$ hydraphile by 16-fold and $C_{14}$ hydraphile by 4-fold (Table 9). When the concentration of hydraphiles was kept constant at 1 µM, a chain length dependent trend was clear (FIG. 15E). $C_{14}$ and $C_{12}$ hydraphiles that could span the membrane were more effective than $C_8$ and $C_{10}$ hydraphiles. Similar results were observed with tetracycline and ciprofloxacin recovery against *K. pnuemoniae* and norfloxacin recovery against *S. aureus* 1199B. The activity of tetracycline was recovered by 40-fold and ciprofloxacin by 10-fold against *K. pneumoniae* (Table 10). Ampicillin activity was not recovered by $C_{14}$ hydraphile against *E. coli* or *K. pneumoniae*. This indicates a mechanism of antibiotic efficacy recovery specific to the inhibition of efflux pump activity.

Figure 15D:
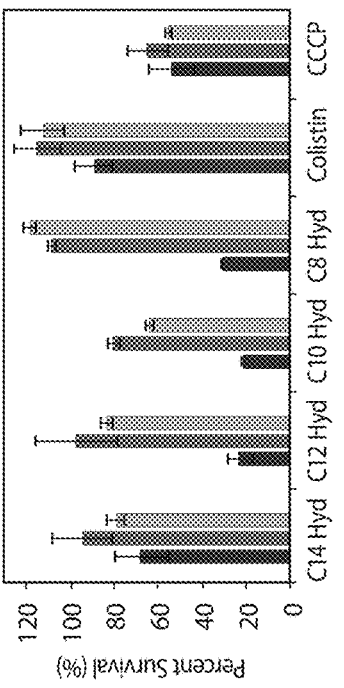
FIG. 15D shows growth curve of $Tet^R$ *E. coli* after treatment with $C_{14}$ hydraphile, tetracycline and their combination. In particular, $C_{14}$ hydraphile at ½ MIC did not affect the growth of tetracycline resistant *E. coli*. The growth rate in the presence of $C_{14}$ hydraphile was similar to that of tetracycline resistant *E. coli* by itself. Tetracycline at 220 μM had minimal effect on the growth of tetracycline resistant *E. coli*. However, when the combination of $C_{14}$ hydraphile and tetracycline was used, the growth of tetracycline resistant *E. coli* was completely inhibited.

Synergy between hydraphiles and tetracycline was confirmed using growth curve and checkerboard experiment (FIG. 15D). In the presence of ½ [MIC] of $C_{14}$ hydraphiles, the lag phase was extended by ~60 minutes. These could be due to either the activity of hydraphiles as ion channels causing disruption of ion gradient homeostasis or due to antimicrobials activity causing cell death. However, the growth of *E. coli* recovered completely and growth rate was the same as that of *E. coli* alone. In the presence of tetracycline, there was some inhibition of growth observed but when ½ [MIC] hydraphile or ¼ [MIC] tetracycline was combined with tetracycline, growth is completely inhibited for over 24 hours. This shows a synergy between $C_{14}$ hydraphiles and the antibiotics.

TABLE 9

Recovery of tetracycline activity against $Tet^R$ *E. coli* by hydraphiles

| Amphiphile used | [Amphiphile] µM | Antibiotic used | [Antibiotic] µM | Fold enhancement |
|---|---|---|---|---|
| No amphiphile | — | Tetracycline | 900 ± 100 | n/a |
| $C_8$ hydraphile | 1 | Tetracycline | 600 ± 100 | 1.5-fold |
| $C_8$ hydraphile | 62.5 (¼[MIC]) | Tetracycline | 82 ± 15 | 11-fold |
| $C_8$ hydraphile | 125 (½[MIC]) | Tetracycline | 30 ± 8 | 30-fold |
| $C_{10}$ hydraphile | 1 | Tetracycline | 600 ± 100 | 1.5-fold |
| $C_{10}$ hydraphile | 8.75 (¼[MIC]) | Tetracycline | 200 ± 20 | 5-fold |
| $C_{10}$ hydraphile | 17.5 (½[MIC]) | Tetracycline | 40 ± 5 | 23-fold |
| $C_{12}$ hydraphile | 1 | Tetracycline | 300 ± 75 | 3-fold |
| $C_{12}$ hydraphile | 1.25 (¼[MIC]) | Tetracycline | 400 ± 50 | 2-fold |
| $C_{12}$ hydraphile | 2.5 (½[MIC]) | Tetracycline | 55 ± 5 | 16-fold |
| $C_{14}$ hydraphile | 0.5 (¼[MIC]) | Tetracycline | 360 ± 40 | 3-fold |
| $C_{14}$ hydraphile | 1 (½[MIC]) | Tetracycline | 220 ± 25 | 4-fold |
| $C_{14}$ hydraphile | 1 (½[MIC]) | Ampicillin | >1000 | 0-fold |

TABLE 10

Recovery of tetracycline activity against *K. pneumoniae* by hydraphiles

| Amphiphile used | [Amphiphile] µM | Antibiotic used | [Antibiotic] µM | Fold enhancement |
|---|---|---|---|---|
| No amphiphile | — | Tetracycline | 1000 ± 100 | n/a |
| $C_8$ hydraphile | 2.5 | Tetracycline | 1000 ± 100 | 1-fold |
| $C_8$ hydraphile | 50 (¼[MIC]) | Tetracycline | 250 ± 50 | 4-fold |
| $C_8$ hydraphile | 100 (½[MIC]) | Tetracycline | 25 ± 10 | 40-fold |
| $C_{10}$ hydraphile | 2.5 | Tetracycline | 900 ± 100 | 1.1-fold |
| $C_{10}$ hydraphile | 14 (¼[MIC]) | Tetracycline | 300 ± 50 | 3-fold |
| $C_{10}$ hydraphile | 28 (½[MIC]) | Tetracycline | 125 ± 25 | 8-fold |
| $C_{12}$ hydraphile | 2.5 | Tetracycline | 500 ± 50 | 2-fold |
| $C_{12}$ hydraphile | 8.75 (¼[MIC]) | Tetracycline | 300 ± 25 | 3-fold |
| $C_{12}$ hydraphile | 17.5 (½[MIC]) | Tetracycline | 125 ± 25 | 8-fold |
| $C_{14}$ hydraphile | 2.5 (¼[MIC]) | Tetracycline | 350 ± 50 | 3-fold |
| $C_{14}$ hydraphile | 5 (½[MIC]) | Tetracycline | 62.5 ± 25 | 16-fold |
| $C_{14}$ hydraphile | 5 (½[MIC]) | Ampicillin | >1000 | 0-fold |

Example 10: Controls

To better understand the recovery of antibiotic efficacy observed with hydraphiles, numerous controls were tested against the same strains of bacteria. First, to see if the structure of hydraphile was important for the observed recovery of antimicrobial efficacy, the recovery of tetracycline activity against Tet$^R$ E. coli was determined using lariat ethers, di benzyl di-aza-crown and quaternary ammonium compounds such as $C_8$ and $C_{12}$ trimethylammoniums. Lariat ethers that differ from hydraphiles because they lack the two distal macrocycles did recover tetracycline activity by 10-fold. Dibenzyl di-aza-crown that has one macrocycle and no alkyl chain linkers did not show any recovery of the tetracycline activity. Among all the structural variations of hydraphiles studied, $C_8$-$C_{14}$ hydraphiles reported herein were the most effective compounds. Tetracycline recovery with $C_8$ and $C_{12}$ trimethylammonium bromides was only 2-4 fold at 128 μM (Table 11), where $C_8$ and $C_{12}$ hydraphile showed 30-fold and 16-fold recovery at ½ MIC concentrations. The results suggest that the structure of hydraphile is important to observe the recovery of antimicrobial activity and it is not just acting as a quaternary ammonium compound that is used as a sterilizing agent in the clinics.

Gramicidin D, valinomycin and Triton X-100 showed only up to 2-fold recovery at concentrations of 20 μM. The concentrations of these compounds were limited by their solubility. The results suggest that the hydraphiles did not act similar to a dimerized ion channel, an ion carrier or a simple detergent. It is noted that a known ion channel that does not require to be dimerized in the membrane of bacteria would be a better control. The use of Colistin and daptomycin is addressed below.

Known efflux pump inhibitors (EPI) CCCP (42 μM) and Reserpine (128 μM) recovered the activity of tetracycline by 4-fold. CCCP dissipates proton motive force required for the transport of antibiotics by the efflux pumps. Even though these EPI showed greater recovery than other controls, they are not as effective as the hydraphiles against Gram-negative bacteria, which make hydraphiles an attractive alternative.

Table 11 represents an important observation. Based on the results of CCCP and reserpine, it was hypothesized that hydraphiles could disrupt the bacteria membrane integrity and/or dissipate the cation gradient required for the transport of antibiotics by active efflux. This hypothesis was tested below.

TABLE 11

Recovery of tetracycline activity against Tet$^R$ E. coli by controls

| Amphiphile used | [Amphiphile] μM | [Tetracycline] μM | Fold enhancement |
| --- | --- | --- | --- |
| No amphiphile | — | 900 ± 100 | n/a |
| Dibenzyl diaza crown | 128 | 900 | 1-fold |
| $C_8$ trimethylammonium bromide | 128 | 450 | 2-fold |
| $C_{12}$ trimethylammonium bromide | 128 | 225 | 4-fold |
| CCCP | 1 | 900 | 1-fold |
| CCCP | 21 | 450 | 2-fold |
| CCCP | 42 | 225 | 4-fold |
| Reserpine | 64 | 450 | 2-fold |
| Reserpine | 128 | 225 | 4-fold |
| Gramicidin D | 20 | 900 ± 100 | 1-fold |
| Valinomycin | 20 | 450 ± 100 | 2-fold |
| Triton X-100 | 20 | 450 ± 100 | 2-fold |
| Triton X-100 | 1700 (0.1%) | 450 ± 100 | 2-fold |

Example 11: Resistance, Cytotoxicity and Bioavailability

Figure 15A:
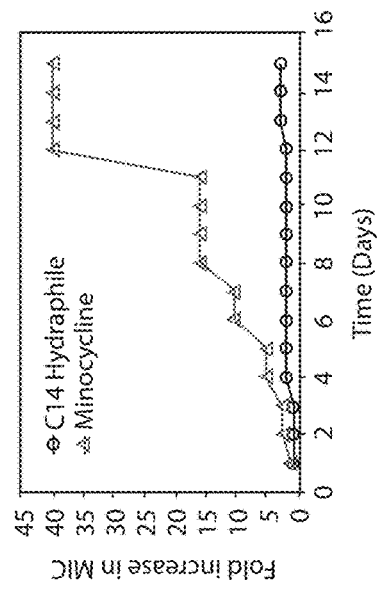
FIGS. 15A/B/C show resistance, cytotoxicity and bioavailability of hydraphiles.
Figure 15C:
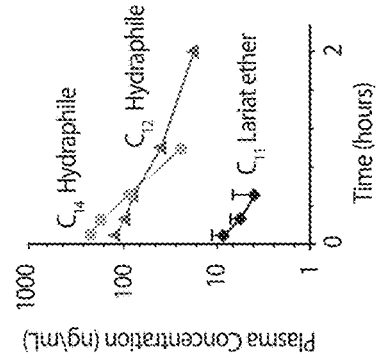
FIG. 15C shows bioavailability of $C_{14}$ hydraphile and $C_{12}$ hydraphile after Sprague Dawley mice were injected intravenously with 0.5 mg/kg of $C_{14}$ hydraphile and $C_{12}$ hydraphile. The bioavailability was observed for over 2 hours.
Figure 15E:
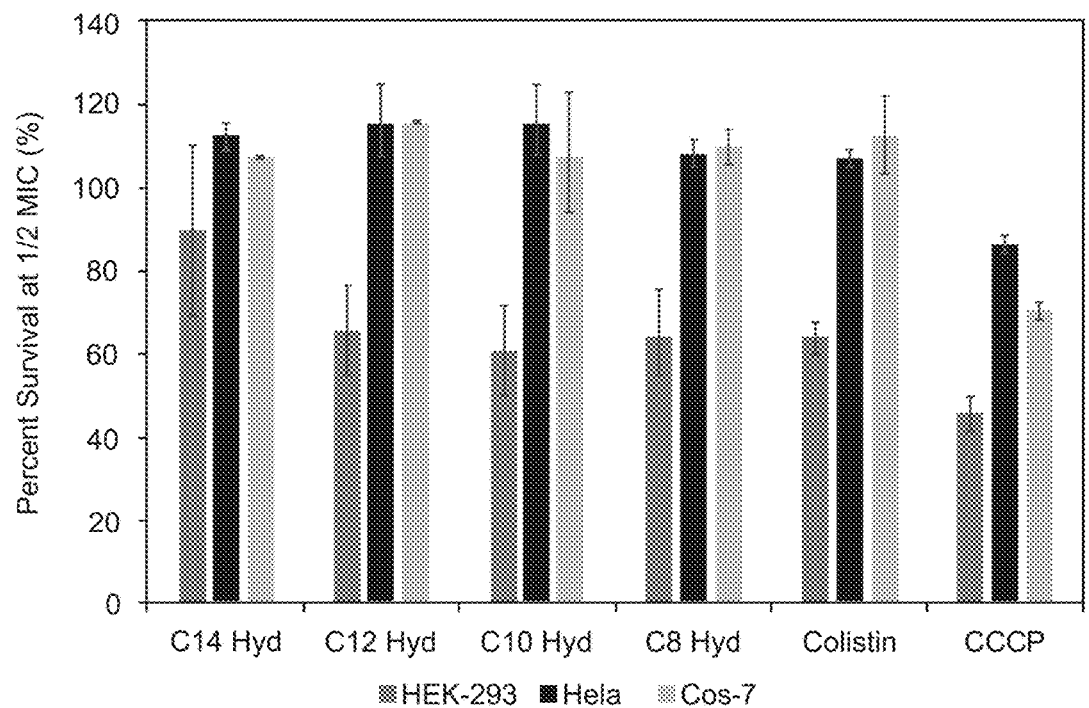
FIG. 15E shows Survival of HEK-293, HeLa and Cos-7 in the presence of ½ MIC of $C_8$-$C_{14}$ hydraphiles.
Figure 15F:
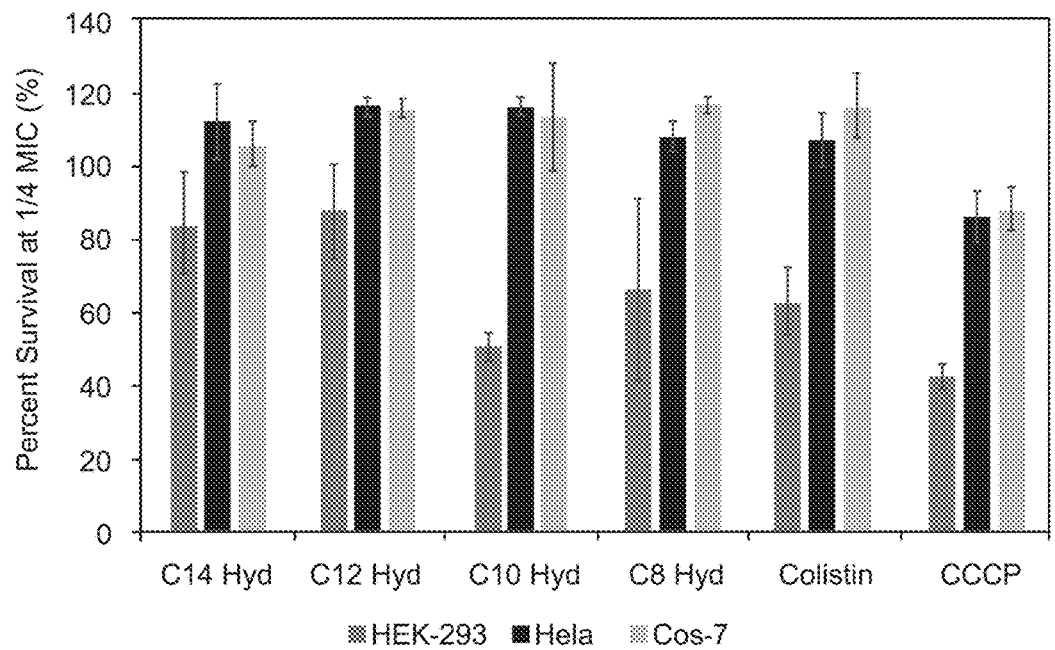
FIG. 15F shows Survival of HEK-293, HeLa and Cos-7 in the presence of ¼ MIC of $C_8$-$C_{14}$ hydraphiles.

Once it was established that the hydraphiles did recover antibiotic efficacy against efflux pump expressing resistant bacteria, the next experiment was to find out if bacteria could develop resistance to the hydraphiles. Sequential culturing method was used to determine if bacteria could develop resistance to the hydraphiles. As seen in FIG. 15A, Tet$^R$ E. coli readily developed resistance to minocycline between 4-6 days. However, the bacteria were not able to develop resistance past 4 μM to $C_{14}$ hydraphile for over 15 days. Hydraphiles are membrane active compounds. Developing resistance to a membrane active compound would require multiple changes in membrane composition/synthesis pathways and is energetically less favorable. Such membrane active compounds are associated with cytotoxicity or mutagenicity.

Recent DNA gel electrophoresis study showed that the hydraphiles at MIC concentrations did not bind DNA. At the concentration of the DNA used for these experiments, hydraphile-DNA complexation was observed, but at much higher concentrations than its MIC. Next, the cytotoxicity of all the hydraphiles used herein was determined against three mammalian epithelial cell lines: HEK-293, HeLa and Cos-7. Colistin and CCCP were used at controls. $C_8$-$C_{12}$ hydraphiles did show cytotoxicity at MIC concentration to the HEK-293 cells. However, $C_{14}$ hydraphile had almost 80% survival against HEK-293 cells at MIC concentration (FIG. 15B). HeLa and Cos-7 showed 80-100% survival against all the hydraphiles used at MIC concentrations. However, at ½ and ¼ the [MIC] of $C_8$-$C_{14}$ hydraphiles used for the synergy study above, minimal cytotoxicity was observed to the HEK-293 cells (FIGS. 15E/15F). CCCP (a known EPI) was cytotoxic to all three cell lines.

FIGS. 15E/15F show the cytotoxicity of $C_8$-$C_{14}$ hydraphiles at ½ and ¼ the MIC against three mammalian epithelial cell lines, HEK-293, HeLa and Cos-7. XTT assay was used to determine the survival of mammalian cells in the presence of synthetic amphiphiles. There was no cytotoxicity by $C_8$-$C_{14}$ hydraphiles against HeLa and Cos-7. A minimal toxicity was observed against HEK-293 cells. Hence, at the sub-MIC concentrations of $C_8$-$C_{14}$ hydraphiles that recovery antimicrobial efficacy against resistant bacteria, the cytotoxicity to mammalian cells is limited. CCCP was used as controls.

One of the issues with amphiphilic molecules to be used as antimicrobials is the bioavailability. It was determined if $C_{14}$ and $C_{12}$ hydraphiles were bioavailable in Sprague Dawley mice after intravenous injections. Specifically, mice were injected with 0.5 mg/kg of $C_{12}$ and $C_{14}$ hydraphiles. The plasma concentration of the compounds was measured every 15 minutes using mass-spectrometry. Both $C_{12}$ and $C_{14}$ hydraphiles were bioavailable in blood plasma for more than 2 hours after at the concentrations of 100-200 ng/mL (~85-170 nM). It is noted that $C_{14}$ hydraphile was found to recover tetracycline activity (in-vitro) against Tet$^R$ E. coli at 500 nM. The use of hydraphile-antibiotic combination was envisioned for treatment of severely ill patients in the ICU, who are infected with MDR bacterial infections. Hence, IV bioavailability of more than 2 hours in plasma is considered optimal.

Example 12: Efflux Pump Inhibition

Figure 16A:
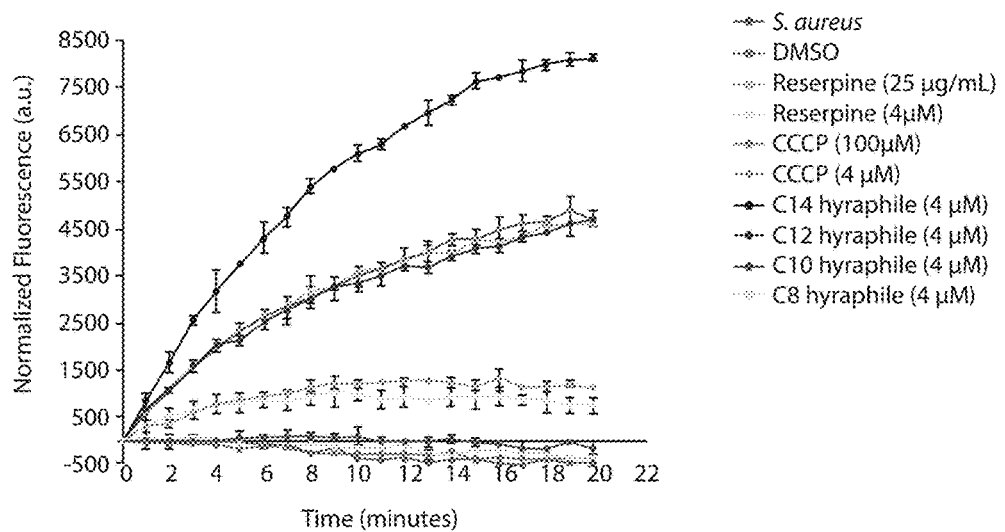
FIGS. 16A/B show that hydraphile inhibits the activity of efflux pumps and increases substrate accumulation in bacteria.

To determine if the activity of efflux pump and accumulation of substrate in the cell cytoplasm was affected by hydraphiles, the *S. aureus* 1199B strain overexpressing the NorA efflux pump was used. Since ethidium bromide (EB) is one of the substrates of the norA efflux pump, fluorescence from DNA-EB complex was utilized to measure effect of hydraphiles on the norA efflux pump. First, EB was added to the *S. aureus* 1199B cells followed by hydraphiles or the controls. If the hydraphiles allows for EB accumulation in the cell cytoplasm, an increase in fluorescence would be expected. The MIC of $C_{14}$ hydraphile was observed at 8 µM against *S. aureus* (O.D. 600 nm=0.7-0.8). As seen in FIG. 16A, after the addition of $C_{14}$ and $C_{12}$ hydraphile (4 µM), the accumulation of EB increases in the cell cytoplasm, regardless of the presence of NorA efflux pumps. Note that the EB accumulation by $C_{12}$ hydraphile at 4 µM was similar to that of known efflux pump inhibitors CCCP (100 µM) and reserpine (25 µg/mL or 42 µM). The accumulation of EB by $C_{14}$ hydraphile (4 µM) was greater than twice as much observed with CCCP and reserpine. However, at 4 µM the activity of CCCP and reserpine was much lower than either $C_{14}$ or $C_{12}$ hydraphiles. $C_8$ and $C_{10}$ hydraphiles (4 µM) did not show any change in the EB accumulation in *S. aureus* 1199B cytoplasm. These hydraphiles with shorter spacer chain lengths do not span the membrane. As indicated by their higher MICs, these compounds might also inhibit the efflux pump activity at higher concentrations. Next step was to determine if the accumulation of EB in the cell cytoplasm was due to the ability of hydraphiles to inhibit the activity of the norA efflux pump or just a simple membrane disruption mechanism.

Figure 16B:
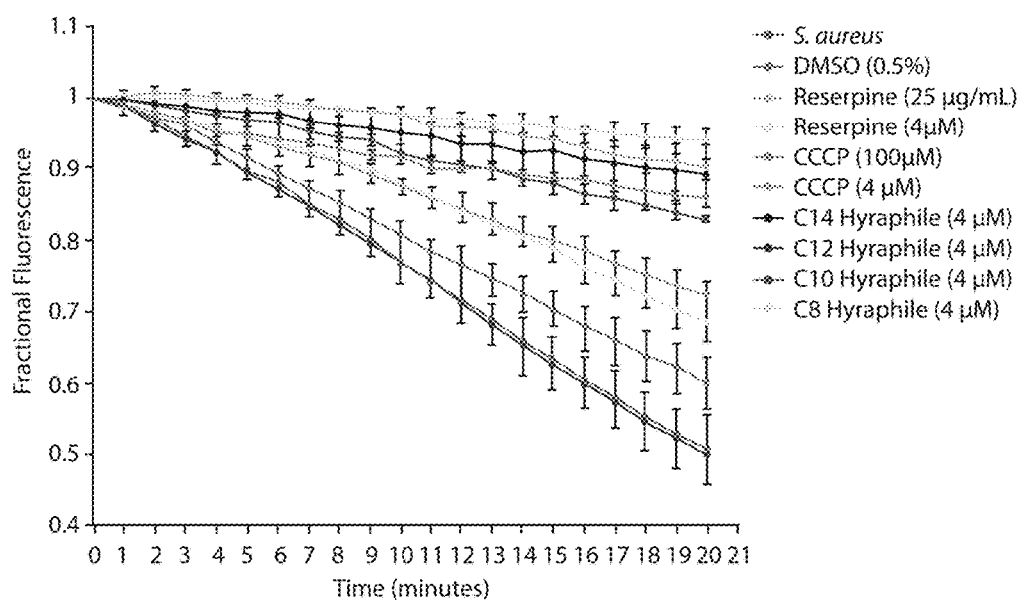
FIG. 16B shows release of ethidium bromide from *S. aureus* 1199B after treatment with reserpine, CCCP, $C_8$-$C_{14}$ hydraphiles (4 μM).

In a following experiment, the ability of hydraphiles to inhibit the activity of efflux pumps was determined. Specifically, the *S. aureus* cells were preloaded with EB using 100 µM CCCP. The cells were washed to remove extracellular EB and CCCP. The cells were then treated with hydraphiles. If hydraphiles inhibit the activity of efflux pumps, then there should be small or no change in fluorescence of EB-DNA complex. As seen in FIG. 16B, in the presence of $C_{10}$-$C_{14}$ hydraphile at 4 µM, there was only minor change in the fluorescence of EB, indicating an inhibition of efflux pump activity. This inhibition was similar to that of known EPI such as CCCP (100 µM) and reserpine (41 µM). When the concentration of CCCP and reserpine was decreased to 4 µM, inhibition of NorA activity was 30% lower than that of hydraphiles. However, if there is no effect of hydraphiles on the efflux pump activity, EB would be released resulting in a decrease in fluorescence. $C_8$ hydraphile had only minor effect on the efflux pump activity at 4 µM. Higher concentrations of $C_8$ hydraphile might have greater effect on efflux pumps. These results confirm the inhibition of efflux pump activity and accumulation of substrate (antibiotics) in cell cytoplasm in the presence of hydraphiles.

Both the accumulation and release of EB from *S. aureus* 1199B in the presence of hydraphiles could be affected by (1) the disruption of membrane integrity, which allows for greater EB accumulation and/or (2) uncoupling of the norA efflux pump from ion gradient caused by non-rectifying channels formed by hydraphiles. It was tested next if membrane permeability of bacterial and mammalian cells was affected by sub-lethal concentrations of hydraphiles. It was also determined if hydraphiles could transport potassium ions from bacteria in the chain length dependent manner.

Example 13: Mechanism of Efflux Pump Inhibition—Ion Transport

Hydraphiles could cause an indirect inhibition of efflux pump activity. Hydraphiles form non-rectifying channels that are specific for specific cations. Such channels could disrupt ion homeostasis that is required by the efflux pump to actively transport antibiotics. $C_8$-$C_{14}$ hydraphiles have been reported to transport sodium and potassium ions from liposomes and mammalian cells. However, they have never been shown to transport cations from bacterial cells.

Figure 17A:
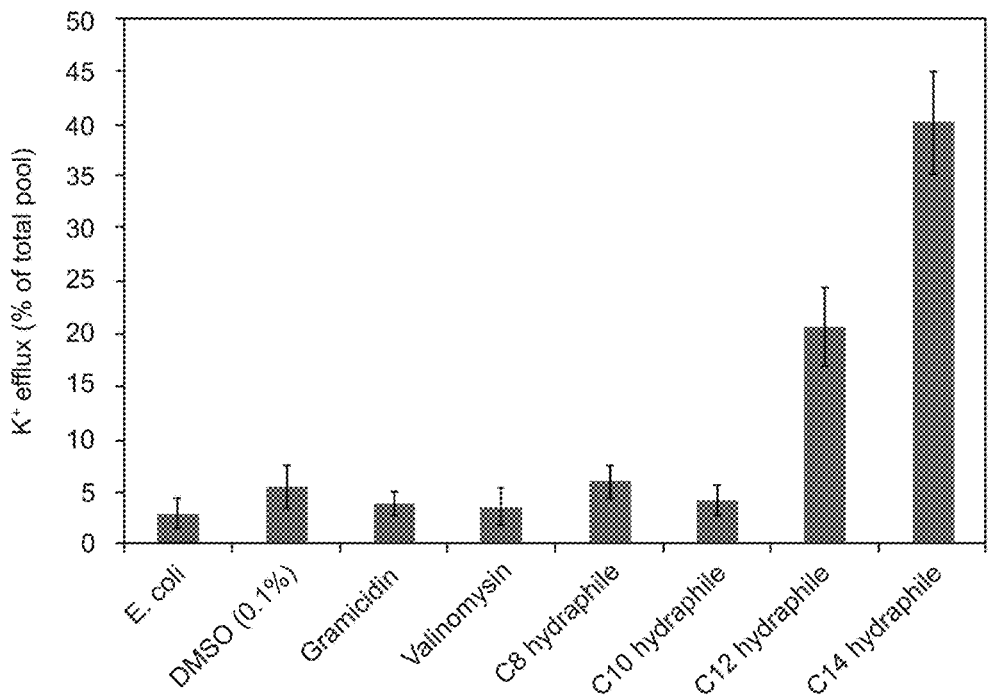
FIGS. 17A/B show release of potassium ions in the presence of $C_8$-$C_{14}$ hydraphiles.

The potassium concentration of *E. coli* cell cytoplasm is 200 mM and that of PBS is 4.15 mM. Hence, when hydraphiles are added to the bacteria and if it forms a non-rectifying channel, the potassium concentration of the media surrounding the *E. coli* cells would increase. This change in potassium ion concentrations was measured using a Potassium selective electrode. Total potassium content of the *E. coli* cells was determined by boiling the cells at 100° C. The results are represented as the percent of total potassium content of *E. coli* released in the presence of hydraphiles or controls (FIG. 17A). Gramicidin D and valinomycin were used as controls. However, the requirement of gramicidin D to dimerize in the bacterial membrane makes an ineffective method for ion transport from bacteria. Valinomycin acts as an ion carrier rather than a channel. Hence, no change in ion transport was observed in its presence. At O.D. 600 nm=1.3, the MIC of $C_{14}$ hydraphile against *E. coli* was 8 µM. The potassium transport ability of $C_8$-$C_{14}$ hydraphiles was then tested at 4 µM. $C_{14}$ and $C_{12}$ hydraphile at 4 µM releases approximately 40% and 25% of the total *E. coli* potassium ion content from cell cytoplasm to the cell surrounding, respectively (FIG. 17A). It is also known that potassium is released when membrane integrity of bacteria is affected. However, a range of studies has been reported that prove hydraphiles' ability to form channels and transport ions. It cannot be distinguished if hydraphiles form channels or disrupt membranes in bacteria. It could be argued that hydraphiles would be toxic due to its ability to disrupt ion gradients. Toxicity studies reported above (FIG. 15B and FIGS. 15E/F) clearly show a minimal cytotoxicity of hydraphiles at sub-MIC concentrations used for the synergy experiments.

Figure 17B:
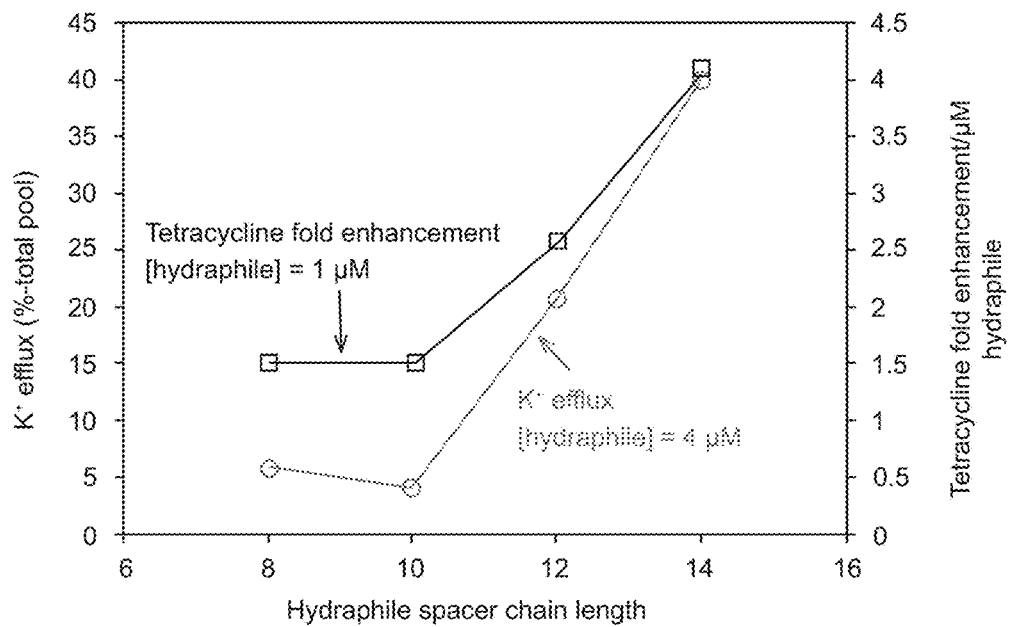
FIG. 17B shows comparison of potassium efflux and recovery of tetracycline activity by $C_8$-$C_{14}$ hydraphiles.

The ion transport ability of hydraphiles was compared to that of tetracycline efficacy recovery against $Tet^R$ *E. coli*. As seen in FIG. 17B, $C_{14}$ and $C_{12}$ hydraphiles are the most efficient compounds at both release of potassium ions and recovery of tetracycline activity. It also became clear that the ion transport from bacteria and increase in antibiotic potency by hydraphiles is dependent on its spacer chain length: $C_{14}$>$C_{12}$>$C_{10}$≥$C_8$. It is possible that $C_{14}$ hydraphile is optimal for hydraphiles to span a bilayer membrane of *E. coli* to perform its function of ion transport and membrane disruption. Using shorter spacer chain length hydraphiles would fail to span the membrane, transport ions or disrupt membrane efficiently. The membrane disruption was tested below.

Example 14: Membrane Disruption

Figure 18A:
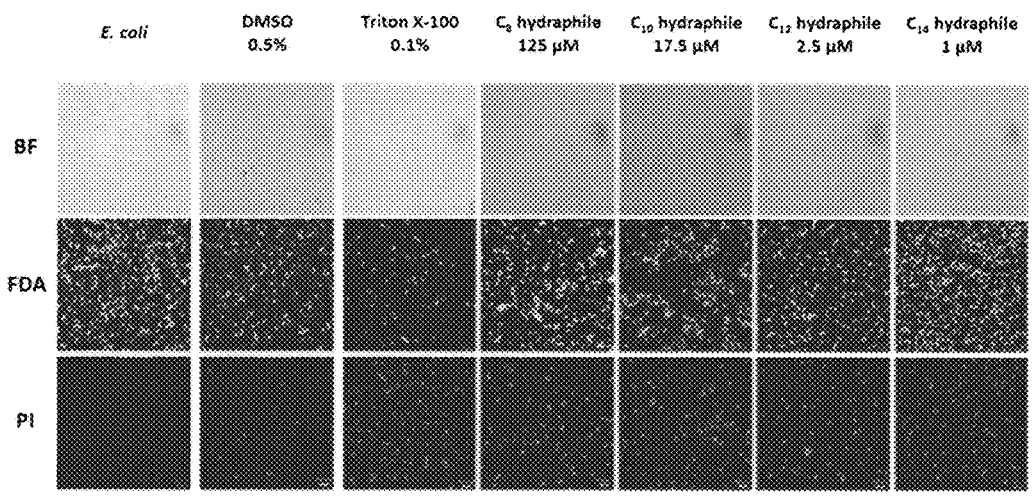
FIG. 18A shows that hydraphiles at ½ MIC concentration increase permeability of $Tet^R$ *E. coli* cells.

A membrane impermeable stain propidium iodide (PI) was used to test the membrane permeability of $Tet^R$ *E. coli* by hydraphiles. The permeability of *E. coli* membrane was tested at ½ MIC of $C_8$-$C_{14}$ hydraphiles. Triton X-100 (0.1% Or 1.6 mM) was used as a control. Fluorescein diacetate (FDA) was used as a cell viability stain. Esterase activity of viable cells converts FDA to a fluorescent fluorescein. Cytoplasmic fluorescence of PI and FDA was observed using a confocal microscope. As seen in FIG. 18A, *E. coli* alone and DMSO control shows maximum viability and minimum membrane disruption. When Triton X-100 was added, the viability decreased and PI fluorescence increased which indicate a membrane disrupting effect of Triton X-100. When $C_8$-$C_{14}$ hydraphiles were added at ½ MIC, most of the cells were viable and membrane integrity was also disrupted as seen by increased PI fluorescence. Here $C_8$ and $C_{10}$ hydraphiles may seem to show greater increase in permeability than $C_{12}$ and $C_{14}$ hydraphiles. This could be due to the fact that ½ MIC of $C_8$ and $C_{10}$ hydraphiles are much higher than other hydraphiles used.

Figure 18B:
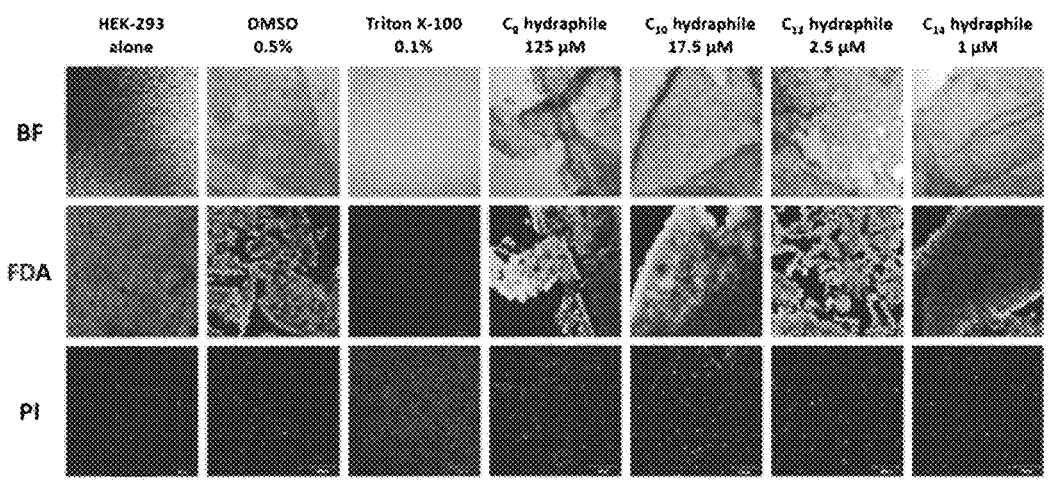
FIG. 18B shows permeability of HEK-293 cells at ½ MIC of hydraphiles.
Figure 18C:
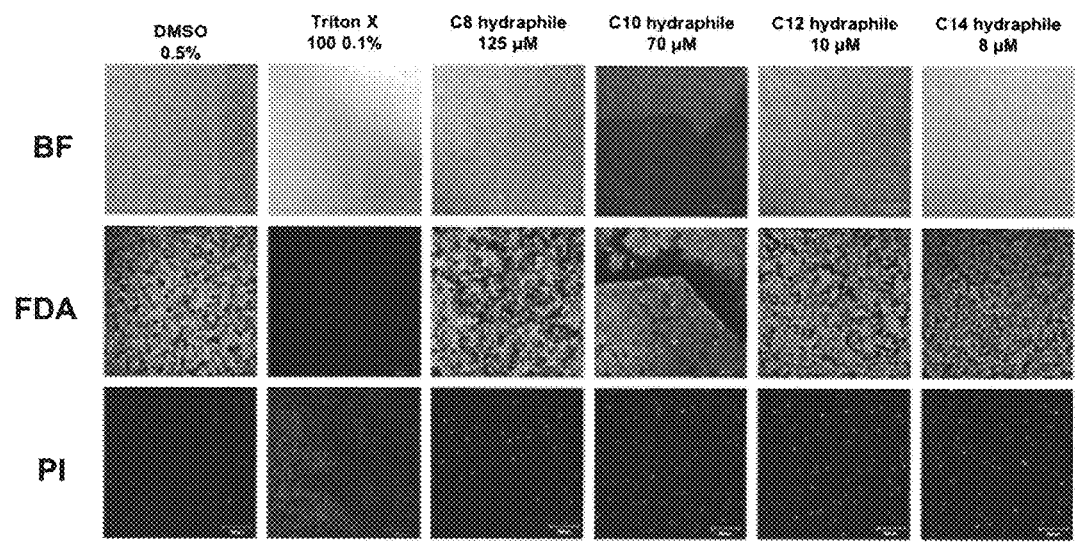
FIG. 18C shows permeability of HEK-293 cells at 2×[MIC] of hydraphiles. In all three figures, top panel shows bright field (BF) images, middle panel shows the cell viability stain fluorescein dicatate (FDA) and the bottom plane shows the membrane permeability stain propidium iodide (PI).

It could be argued that hydraphiles could also localize and disrupt the mammalian cell membranes. The effect of $C_8$-$C_{14}$ hydraphiles on the membrane integrity of mammalian HEK-293 cells was then tested, see, FIGS. 18B-18C, which demonstrate the permeability of HEK-293 mammalian cells in the presence of ½ MIC and 2 [MIC] of $C_8$-$C_{14}$ hydraphiles. These hydraphiles increased the permeability of *E. coli* cells at ½ MIC concentrations. However, they failed to increase the permeability of HEK-293 mammalian cells at 2×[MIC] concentrations. At 0.1% or 1.6 mM, Triton X-100 killed all the HEK-293 cells and disrupted membranes showing high PI fluorescence. However, the viability was high and minimal PI fluorescence was observed with ½ MICs of $C_8$-$C_{14}$ hydraphiles. The results show that at ½ MIC the hydraphiles disrupted bacterial membrane but did not affect mammalian membranes. It was confirmed that even at MIC concentrations, the hydraphiles failed to affect the HEK-293 mammalian cell membrane integrity. It is concluded that $C_8$-$C_{14}$ hydraphiles can selectively increase the permeability of bacterial cells without affecting the permeability of mammalian cells. $C_8$ hydraphile was not used beyond 125 μM for solubility reasons. DMSO and Triton X-100 were used as controls.

Figure 19:
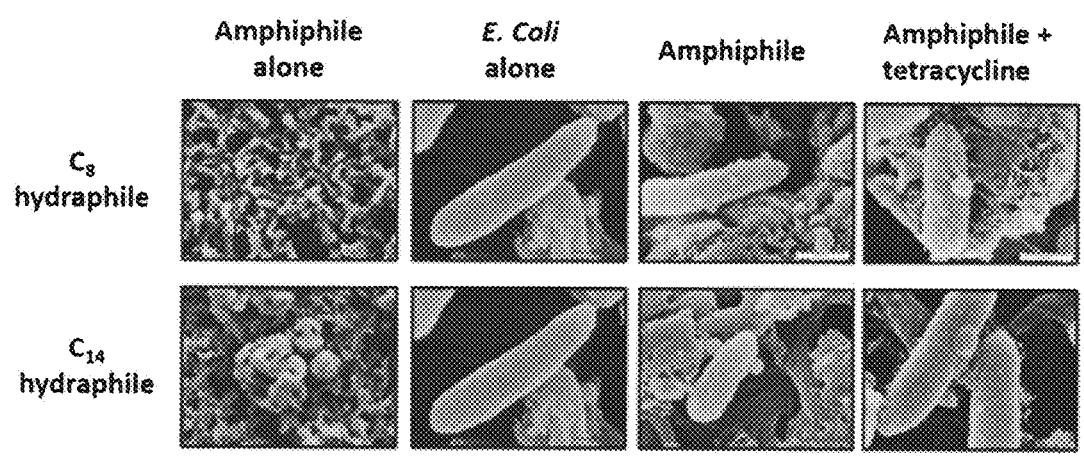
FIG. 19 shows scanning electron microscopy of $C_8$ and $C_{14}$ hydraphile treated cells. Top panel shows the $C_8$ hydraphiles treated cells and bottom panel shows $C_{14}$ hydraphile treated cells. Amphiphile alone column on the left shows an image of background membrane (top) and hydraphile aggregate (bottom). Hydraphiles form aggregates and membrane blisters on the *E. coli* surface.

To confirm if $C_8$ and $C_{14}$ hydraphile both affect the membrane integrity of individual bacterial cells, scanning electron microscopy was used. Specifically, the Tet$^R$ *E. coli* cells were treated with ½ MIC of $C_8$ and $C_{14}$ hydraphiles, loaded on to a membrane, fixed and stained before observing under a SEM (FIG. 19). Under the amphiphile alone column, membrane background (top) and an aggregate formed by $C_{14}$ hydraphiles in the absence of bacteria was observed. Similar aggregates were observed with $C_8$ hydraphiles. In an untreated *E. coli* cell, the membrane was corrugated and no membrane disruption or aggregates were apparent. When the *E. coli* was treated with hydraphile alone or hydraphile+tetracycline, the following three key features were observed with both $C_8$ and $C_{14}$ hydraphiles.

First, uniform, well-formed aggregates of hydraphiles of approximately 100-120 nm was observed on the surface of *E. coli* (FIG. 20A). Hydraphiles may form uniform 100-200 nm aggregates before attaching and inserting to the *E. coli* membranes. Alternatively, these aggregates may have also formed after the disruption of *E. coli* membrane. In such case, these aggregates may comprise of a mixture of *E. coli* membrane lipids and hydraphiles. Secondly, irregular blisters were observed on the surface of *E. coli* membranes (FIG. 20B). These blisters were distinct from the hydraphile aggregates observed next to the blisters on the bacteria. It is known that if cytoplasmic membrane is disrupted, the cytosolic content is released in the periplasmic space, forming a blister/bulge of the outer membrane. Hence, hydraphiles that disrupted the inner membrane could've formed the blisters from the outer membrane. Lastly, some bacteria were observed with membrane smoothening (FIG. 20C). It is known that under osmotic stress the water uptake by bacteria could cause swelling of the bacterial cell. This swelling would cause the corrugated membrane to stretch and become smooth. Taken together, these images show that hydraphiles form aggregates that attach to the bacteria surface. The hydraphiles could both transport ion as observed with membrane smoothening and disrupt membranes as observed with membrane blisters.

Having illustrated and described the principles of the present invention, it should be apparent to persons skilled in the art that the invention can be modified in arrangement and detail without departing from such principles. Those skilled in the art will recognize, or be able to ascertain using no more than routine experimentation, many equivalents to the specific embodiments of the invention described herein. Such equivalents are intended to be encompassed by the following claims.

All publications and published patent documents cited in this specification are incorporated herein by reference to the same extent as if each individual publication or patent application was specifically and individually indicated to be incorporated by reference.

What is claimed is:

1. A method of reversing the resistance of a multi-drug resistant bacterium to an antibiotic by inhibiting efflux pump activity in the multi-drug resistant bacterium, said method comprising administering to said bacterium the antibiotic and a synthetic amphiphile, wherein said synthetic amphiphile is a hydraphile comprising the structure of Formula 4;

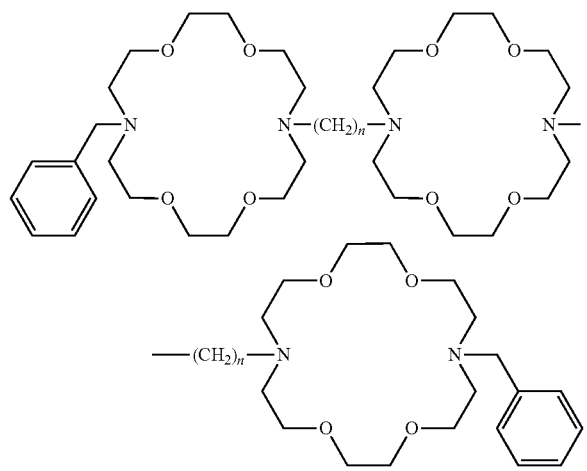

Formula 4 wherein n is 8, 10, 12, or 14; and wherein said hydraphile is administered at a concentration of half or less of its minimum inhibitory concentration (MIC) against the multi-drug resistant bacterium as determined in the absence of the antibiotic.

2. The method of claim 1, wherein said synthetic amphiphile is administered as an aggregate or in a liposome.

3. The method of claim 1, wherein said synthetic amphiphile is administered in a protonated or salt form.

4. The method of claim 1, wherein said bacterium is a bacterium in the family Enterobacteriaceae, in the family Bacillaceae, or in the family Pseudomonadaceae.

5. The method of claim 4, wherein said bacterium is an efflux pump expressing Gram-positive or Gram-negative bacterium.

6. The method of claim 1, wherein the antibiotic is administered at a concentration lower than its minimum inhibitory concentration (MIC) against the multi-drug resistant bacterium as determined in the absence of the synthetic amphiphile.

7. The method of claim 1, wherein the hydraphile is administered at a concentration of 1 nM to 10 µM.

8. The method of claim 6, wherein the hydraphile is administered at a concentration of 1 nM to 10 µM.

* * * * *